(12) United States Patent
Muir et al.

(10) Patent No.: US 9,765,154 B2
(45) Date of Patent: Sep. 19, 2017

(54) PHOSPHOHISTIDINE ANALOGS

(71) Applicant: THE ROCKEFELLER UNIVERSITY, New York, NY (US)

(72) Inventors: Tom W. Muir, Princeton, NJ (US); Jung-Min Kee, Plainsboro, NJ (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 14/708,677

(22) Filed: May 11, 2015

(65) Prior Publication Data
US 2015/0344589 A1    Dec. 3, 2015

Related U.S. Application Data

(62) Division of application No. 13/825,699, filed as application No. PCT/US2011/052854 on Sep. 23, 2011, now Pat. No. 9,035,068.

(60) Provisional application No. 61/386,424, filed on Sep. 24, 2010.

(51) Int. Cl.
| C07K 16/44 | (2006.01) |
| A61K 31/675 | (2006.01) |
| C07F 9/6518 | (2006.01) |
| A61K 47/48 | (2006.01) |
| C07D 249/04 | (2006.01) |
| C07F 9/40 | (2006.01) |

(52) U.S. Cl.
CPC ............ *C07K 16/44* (2013.01); *A61K 31/675* (2013.01); *A61K 47/4833* (2013.01); *A61K 47/48061* (2013.01); *C07F 9/65182* (2013.01); *C07F 9/65186* (2013.01); *C07D 249/04* (2013.01); *C07F 9/4015* (2013.01); *C07K 2317/34* (2013.01)

(58) Field of Classification Search
CPC ............ A61K 31/675; A61K 47/48061; A61K 47/4833; C07F 9/65186; C07F 9/65182; C07F 9/4015; C07K 16/44; C07K 2317/34; C07D 249/04
See application file for complete search history.

(56) References Cited

U.S. PATENT DOCUMENTS

| 3,213,103 | A | 10/1965 | Bernardus Gerhardus van den Bos |
| 3,898,229 | A | 8/1975 | Kristinsson et al. |
| 5,453,417 | A | 9/1995 | Lougheed |
| 5,599,681 | A | 2/1997 | Epstein et al. |
| 5,807,999 | A | 9/1998 | Kohtz |
| 6,156,784 | A | 12/2000 | Betageri et al. |
| 6,824,994 | B2 | 11/2004 | Weisblum et al. |
| 7,049,080 | B2 | 5/2006 | Kramer et al. |
| 7,183,385 | B2 | 2/2007 | Comb et al. |
| 7,279,299 | B2 | 10/2007 | Luche et al. |
| 7,371,829 | B2 | 5/2008 | McConnell et al. |
| 2003/0224447 | A1 | 12/2003 | McConnell et al. |
| 2006/0141549 | A1 | 6/2006 | Mahajan et al. |
| 2006/0153825 | A1 | 7/2006 | Kellner et al. |
| 2006/0286611 | A1 | 12/2006 | Zempleni et al. |
| 2007/0160989 | A1 | 7/2007 | Bawden et al. |
| 2008/0003608 | A1 | 1/2008 | Febitha et al. |
| 2009/0263879 | A1 | 10/2009 | Chang et al. |

OTHER PUBLICATIONS

Frackelton et al. Characterization and use of monoclonal antibodies for isolation of phosphotyrosyl proteins from retrovirus transformed cells and growth factor-stimulated cells. Molecular and Cellular Biology 1983, vol. 3, No. 8, pp. 1343-1352.*
Hollinger et al. Engineered antibody fragments and the rise of single domains. Nature Biotechnology 2005, vol. 23, No. 9, pp. 1126-1136.*
Besant, R G., et al., "Detection and analysis of protein histidine phosphorylation" Mol Cel Biochem 329:93-106 (2009).
Cruz, E., "Ruthenium in Organic Synthesis: Outline" 1-14 (2004).
Frackelton, A. R., et al., "[8] Generation of Monoclonal Antibodies against Phosphotyrosine and Their Use for Affinity Purification of Phosphotyrosine-Containing Proteins" Methods in Enzymology, 201:79-92 (1991).
Gajewski, M., et al., "Design, synthesis, and biological activity of novel triazole animo acids used to probe binding interactions between ligand and neutral amino acid transport protein SN1" Bioorganic & Medicinal Chemistry Letters 17:4163-4166 (2007).
International Search Report and Written Opinion issued in PCT/US2011/052854 dated Apr. 25, 2012.
Joseph, S. K., et al. "Hydrolysis of inositol phosphates by plant cell extracts" Biochem. J. 264:851-856 (1989).
Kee, J., et al., "Development of Stable Phosphohistidine Analogues" J. Am. Chem. 132(41):14327-24329 (2010).

(Continued)

*Primary Examiner* — Shafiqul Haq
(74) *Attorney, Agent, or Firm* — Scully Scott Murphy and Presser

(57) ABSTRACT

The present invention relates to the phosphohistidine analogs of the present invention which of the formula

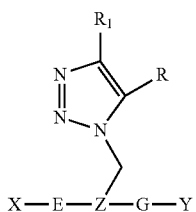

and the hapten containing the residue of same. It also relates to the hapten conjugated to a carrier molecule and the isolated antibodies raised against the immunogens, said antibodies recognizing polypeptide containing a phosphorylated histidine or the phosphotriazole residue but it does not recognize an amino acid or polypeptide that is not phosphorylated or a polypeptide which is phosphorylated on amino acids other than histidine but not on histidine.

15 Claims, 11 Drawing Sheets

(56) References Cited

OTHER PUBLICATIONS

Kehoe, J. W., et al., "Using Phage Display to Select Antibodies Recognizing Post-translational Modifications Independently of Sequence Context" Molecular & Cellular Proteomics 5:2350-2363 (2005).
Mc Allister, T. E., et al., "Fmoc-chemistry of a stable phosphohistidine analogue" Chemi. Commun. 47:1297-1299 (2011).
McGinty, R. K. et al. "Chemically ubiquitylated histone H2B stimulates hDot1L-mediated intranucleosomal methylation" Nature 453: 812-816 plus 3 pages additional pages (2008).
Olson, J.S.C., et al.. "Assays for Determination of Protein Concentration" Current Protocols in Protein Science Supplement 48:3.4.1-3.4.29 (2007).
Pirrung, M. C., et al., "Thiophosphorylation of Histidine" J. Org. Chem. 65:8448-8453 (2000).
Sblattero, D., et al., "Exploiting recombination in single bacteria to make large phage antibody libraries" Nature Biotechnology 18:75-80 (2000).
Schenkels, C., et al., "Phosphofurylalanine, a Stable Analog of Phosphohistidine" Bioorganic & Medicinial Chemistry Letters 9:1443-1446 (1999).
Shogren-Knaak, M., et al., "Histone H4-K16 Acetylation Controls Chromation Structure and Protein Interactions" Science 311:844-847 (2006).
Smith, G. P., et al., "Phage Display" Chem. Rev. 97:391-410 (1997).
Regitz, 1985, Synthesis, vol. 2, p. 178-180.

\* cited by examiner

SEQUENCE LISTING

```
<160> NUMBER OF SEQ ID NOS: 24

<210> SEQ ID NO 1
<211> LENGTH: 11
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: AMIDATION
<220> FEATURE:
<221> NAME/KEY: MOD_RES
<222> LOCATION: (4)..(4)
<223> OTHER INFORMATION: ACETYLATION
<220> FEATURE:
<221> NAME/KEY: MISC_FEATURE
<222> LOCATION: (6)..(6)
<223> OTHER INFORMATION: 3-phosphoryltriazolylalaninyl

<400> SEQUENCE: 1

Cys Gly Ala Lys Arg Xaa Arg Lys Val Leu Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: 3-phosphoryltriazolylalaninyl
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (11)..(11)
<223> OTHER INFORMATION: AMIDATION

<400> SEQUENCE: 2

Cys Gly Ala Lys Arg Xaa Arg Lys Val Leu Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(7)
<223> OTHER INFORMATION: 3-phosphoryltriazolylalaninyl
<220> FEATURE:
<221> NAME/KEY: MOD_RES
<222> LOCATION: (12)..(12)
<223> OTHER INFORMATION: AMIDATION

<400> SEQUENCE: 3

Cys Val Arg Tyr Thr Glu Xaa Ala Lys Arg Lys Thr
1               5                   10

<210> SEQ ID NO 4
<211> LENGTH: 11
<212> TYPE: PRT
<213> ORGANISM: Artificial Sequence
```

```
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: 3-phosphoryltriazolylalaninyl
<220> FEATURE:
<221> NAME/KEY: MOD_RES
<222> LOCATION: (11)..(11)
<223> OTHER INFORMATION: AMIDATION

<400> SEQUENCE: 4

Cys Arg Asn Ile Ile Xaa Gly Ser Asn Ser Val
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: ACETYLATION
<220> FEATURE:
<221> NAME/KEY: MISC_FEATURE
<222> LOCATION: (6)..(6)
<223> OTHER INFORMATION: 1-phosphoryltriazolylalaninyl
<220> FEATURE:
<221> NAME/KEY: MOD_RES
<222> LOCATION: (11)..(11)
<223> OTHER INFORMATION: AMIDATION

<400> SEQUENCE: 5

Cys Gly Ala Lys Arg Xaa Arg Lys Val Leu Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: 1-phosphoryltriazolylalaninyl
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (11)..(11)
<223> OTHER INFORMATION: AMIDATION

<400> SEQUENCE: 6

Cys Gly Ala Lys Arg Xaa Arg Lys Val Leu Arg
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(7)
<223> OTHER INFORMATION: 1-phosphoryltriazolylalaninyl
<220> FEATURE:
<221> NAME/KEY: MOD_RES
<222> LOCATION: (12)..(12)
<223> OTHER INFORMATION: AMIDATION

<400> SEQUENCE: 7

Cys Val Thr Tyr Thr Glu Xaa Ala Lys Arg Lys Thr
1               5                  10

<210> SEQ ID NO 8
<211> LENGTH: 11
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: 1-phosphoryltriazolylalaninyl
<220> FEATURE:
<221> NAME/KEY: MOD_RES
<222> LOCATION: (11)..(11)
<223> OTHER INFORMATION: AMIDATION

<400> SEQUENCE: 8

Cys Arg Asn Ile Ile Xaa Gly Ser Asp Ser Val
1               5                  10

<210> SEQ ID NO 9
<211> LENGTH: 5
<212> TYPE: PRT
<213> ORGANISM: Artificial Sequence
<220> FEATURE:
<223> OTHER INFORMATION: peptide intermediary with mbha resin
<220> FEATURE:
<221> NAME/KEY: MISC_FEATURE
<222> LOCATION: (5)..(5)
<223> OTHER INFORMATION: mbha resin through amino bridge

<400> SEQUENCE: 9

Arg Lys Val Leu Arg
1               5

<210> SEQ ID NO 10
<211> LENGTH: 5
<212> TYPE: PRT
<213> ORGANISM: Artificial Sequence
<220> FEATURE:
<223> OTHER INFORMATION: peptide intermediary with mbha resin
<220> FEATURE:
<221> NAME/KEY: MISC_FEATURE
<222> LOCATION: (1)..(1)
<223> OTHER INFORMATION: 2-tert-butoxycarbonylamino-3-(4-
      diethoxyphosphoryl-1H-1,2,3-triazol-1-yl)-propanoyl
<220> FEATURE:

<221> NAME/KEY: MISC_FEATURE
<222> LOCATION: (5)..(5)
<223> OTHER INFORMATION: mbha resin through amino bridge

<400> SEQUENCE: 10

Arg Leu Val Lys Arg
1               5

<210> SEQ ID NO 11
<211> LENGTH: 5
<212> TYPE: PRT
<213> ORGANISM: Artificial Sequence
<220> FEATURE:
<223> OTHER INFORMATION: peptide intermediary with mbha resin
<220> FEATURE:
<221> NAME/KEY: MISC_FEATURE
<222> LOCATION: (1)..(1)
<223> OTHER INFORMATION: 2-tert-butoxycarbonylamino-3-(5-
      diethoxyphosphoryl)-1H-1,2,3-triazol-1-yl)-propanoyl
<220> FEATURE:
<221> NAME/KEY: MISC_FEATURE
<222> LOCATION: (5)..(5)
<223> OTHER INFORMATION: mbha resin through amino bridge

<400> SEQUENCE: 11

Arg Leu Val Lys Arg
1               5

<210> SEQ ID NO 12
<211> LENGTH: 11
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: 3-(4-phosphoryl-1H,-1,2,3- triazol-1-yl)-
      propanoyl
<220> FEATURE:
<221> NAME/KEY: MOD_RES
<222> LOCATION: (11)..(11)
<223> OTHER INFORMATION: AMIDATION

<400> SEQUENCE: 12

Cys Gly Ala Lys Arg Xaa Arg Lys Val Leu Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: 3-(5-phosphoryl-1-H-1,2,3-triazol-1-yl)-
      propanoyl
<220> FEATURE:
<221> NAME/KEY: MOD_RES
<222> LOCATION: (11)..(11)
<223> OTHER INFORMATION: AMIDATION

<400> SEQUENCE: 13

```
Cys Gly Ala Lys Arg Xaa Arg Lys Val Leu Arg
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Histidine containing peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (11)..(11)
<223> OTHER INFORMATION: AMIDATION

<400> SEQUENCE: 14

Cys Gly Ala Lys Arg His Arg Lys Val Leu Arg
1               5                   10

<210> SEQ ID NO 15
<211> LENGTH: 11
<212> TYPE: PRT
<213> ORGANISM: Artificial Sequence
<220> FEATURE:
<223> OTHER INFORMATION: peptide containing Phosphophenylalanine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Phosphorylation
<220> FEATURE:
<221> NAME/KEY: MOD_RES
<222> LOCATION: (11)..(11)
<223> OTHER INFORMATION: AMIDATION

<400> SEQUENCE: 15

Cys Gly Ala Lys Arg Phe Arg Lys Val Leu Arg
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Peptide containing Phosphoserine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: phosphorylation
<220> FEATURE:
<221> NAME/KEY: MOD_RES
<222> LOCATION: (11)..(11)
<223> OTHER INFORMATION: AMIDATION

<400> SEQUENCE: 16

Cys Gly Ala Lys Arg Ser Arg Lys Val Leu Arg
1               5                   10

<210> SEQ ID NO 17
<211> LENGTH: 11
<212> TYPE: PRT
```

```
<213> ORGANISM: Artificial Sequence
<220> FEATURE:
<223> OTHER INFORMATION: peptide containing Phosphothreonine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Phosphorylation
<220> FEATURE:
<221> NAME/KEY: MOD_RES
<222> LOCATION: (11)..(11)
<223> OTHER INFORMATION: AMIDATION

<400> SEQUENCE: 17

Cys Gly Ala Lys Arg Thr Arg Lys Val Leu Arg
1               5                   10

<210> SEQ ID NO 18
<211> LENGTH: 22
<212> TYPE: PRT
<213> ORGANISM: Artificial Sequence
<220> FEATURE:
<223> OTHER INFORMATION: Phosphohistidine analog
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (18)..(18)
<223> OTHER INFORMATION: phosphoryltriazolylalaninyl
<220> FEATURE:
<221> NAME/KEY: MISC_FEATURE
<222> LOCATION: (21)..(21)
<223> OTHER INFORMATION: amidoethylthio

<400> SEQUENCE: 18

Ser Gly Arg Gly Lys Gly Gly Lys Gly Leu Gly Lys Gly Gly Ala Lys
1               5                   10                  15

Arg Xaa Arg Lys Val Leu
            20

<210> SEQ ID NO 19
<211> LENGTH: 41
<212> TYPE: DNA
<213> ORGANISM: Artificial Sequence
<220> FEATURE:
<223> OTHER INFORMATION: reverse primer for Phosphohistidine analogs

<400> SEQUENCE: 19
gtcacgcaga actttacgcg cacgtttagc accaccttta c                   41

<210> SEQ ID NO 20
<211> LENGTH: 40
<212> TYPE: DNA
<213> ORGANISM: Artificial Sequence
<220> FEATURE:
<223> OTHER INFORMATION: Forward primer for Phosphohistidine analogs

<400> SEQUENCE: 20
tgacgctgtt acctacaccg aagccgctaa acgtaaaacc                     40

<210> SEQ ID NO 21
<211> LENGTH: 40
<212> TYPE: DNA
<213> ORGANISM: Artificial Sequence
<220> FEATURE:
```

<223> OTHER INFORMATION: reverse primer for Phosphohistidine analogs

<400> SEQUENCE: 21

```
ggttttacgt ttagcggctt cggtgtaggt aacagcgtca                    40
```

<210> SEQ ID NO 22
<211> LENGTH: 79
<212> TYPE: PRT
<213> ORGANISM: Artificial Sequence
<220> FEATURE:
<223> OTHER INFORMATION: intermediary for peptide ligation
<220> FEATURE:
<221> NAME/KEY: MISC_FEATURE
<222> LOCATION: (1)..(1)
<223> OTHER INFORMATION: 3-thiol-2-amino-propanoyl

<400> SEQUENCE: 22

```
Cys Asp Asn Ile Gln Gly Ile Thr Lys Pro Ala Ile Arg Arg Leu Ala
1               5                   10                  15

Arg Arg Gly Gly Val Arg Ile Ser Gly Leu Ile Tyr Glu Glu Thr Arg
            20                  25                  30

Gly Val Leu Lys Val Phe Leu Glu Asn Val Ile Arg Asp Ala Val Thr
        35                  40                  45

Tyr Thr Glu His Ala Lys Arg Lys Thr Val Thr Ala Met Asp Val Val
    50                  55                  60

Tyr Ala Leu Lys Arg Gln Gly Arg Thr Leu Tyr Gly Glu Gly Gly
65                  70                  75
```

<210> SEQ ID NO 23
<211> LENGTH: 101
<212> TYPE: PRT
<213> ORGANISM: Artificial Sequence
<220> FEATURE:
<223> OTHER INFORMATION: full length Phosphohistidine analogs
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (18)..(18)
<223> OTHER INFORMATION: phosphoryltriazolylalaninyl
<220> FEATURE:
<221> NAME/KEY: MISC_FEATURE
<222> LOCATION: (22)..(22)
<223> OTHER INFORMATION: 3-thiol-propanoyl

<400> SEQUENCE: 23

```
Ser Gly Arg Gly Lys Gly Gly Lys Gly Leu Gly Lys Gly Gly Ala Lys
1               5                   10                  15

Arg Xaa Arg Lys Val Leu Cys Asp Asn Ile Gln Gly Ile Thr Lys Pro
            20                  25                  30

Ala Ile Arg Arg Leu Ala Arg Arg Gly Gly Val Arg Ile Ser Gly Leu
        35                  40                  45

Ile Tyr Glu Glu Thr Arg Gly Val Leu Lys Val Phe Leu Glu Asn Val
    50                  55                  60

Ile Arg Asp Ala Val Thr Tyr Thr Glu His Ala Lys Arg Lys Thr Val
65                  70                  75                  80

Thr Ala Met Asp Val Val Tyr Ala Leu Lys Arg Gln Gly Arg Thr Leu
                85                  90                  95

Tyr Gly Glu Gly Gly
            100
```

```
<210> SEQ ID NO 24
<211> LENGTH: 41
<212> TYPE: DNA
<213> ORGANISM: Artificial Sequence
<220> FEATURE:
<223> OTHER INFORMATION: forward primer for Phosphohistidine analogs

<400> SEQUENCE: 24
gtaaaggtgg tgctaaacgt gcgcgtaaag ttctgcgtga c                          41
```

PHOSPHOHISTIDINE ANALOGS

CROSS REFERENCE TO RELATED APPLICATION

The present application is a divisional application of U.S. patent application Ser. No. 13/825,699 filed on Jun. 11, 2013, which is a '371 of PCT Application No. US2011/52854 filed on Sep. 23, 2011, which claims benefit of U.S. Provisional Patent Application No. 61/386,424 filed on Sep. 24, 2010.

STATEMENT OF GOVERNMENT INTEREST

The work leading to the invention was made in part with United States Government funds from the U.S. National Institutes of Health under Contract Nos. GM086868 and RC2CA148354. Therefore the U.S. Government has certain rights in the invention.

INCORPORATION BY REFERENCE OF SEQUENCE LISTING

The Sequence Listing in the ASCII text file, named as 26298_SEQ1to24_ST25.txt of 11 KB, created on Mar. 12, 2015, and submitted to the United States Patent and Trademark Office via EFS-Web, is incorporated herein by reference."

NATURE OF THE INVENTION

The present invention relates to phosphohistidine analogs that are useful for the preparation of immunogens, haptens containing said phosphohistidine analogs, immunogens comprised of these haptens linked to carrier molecules, antibodies thereto and uses of these antibodies, haptens, immunogens and phosphohistidine analogs.

BACKGROUND OF THE INVENTION

Protein phosphorylation is one of the most common and extensively studied posttranslation modifications (PTMs). Phosphorylation and dephosphorylation of proteins control the function of the target protein, and their misregulation has been linked to many diseases, including cancer. Accordingly, protein kinases and phosphatases have emerged as important drug targets, boosted by the prominent success of Gleevec®, a tyrosine kinase inhibitor used to treat leukemia and other malignancies.

While most studies on protein phosphorylation have focused on the 0-phosphorylation of Ser, Thr and Tyr residues, very little is known about histidine phosphorylation, which occurs at the imidazole nitrogens. The role of the histidine phosphorylation, however, is well documented in bacterial two-component signaling pathways; yet proteins with phosphohistidine (pHis) residues are also found in eukaryotic cells. In fact, in *Physarum polycephalum*, pHis accounts for 6% of the total phosphonoamino acids in its basic nuclear proteins. The prevalence of pHis is strikingly high among these proteins, considering that phosphotyrosine (pTyr) is found in less than 1% of eukaryotic cellular phosphoproteins.

Histidine phosphorylation plays an important role in cell processes. For example, histidine phosphorylation plays an important role in the signaling processes of higher eukaryotes. Further, the modification has been implicated in several processes, including G-protein signaling, ion conduction, secondary metabolism and chromatin biology. It is known that a histidine Kinase, nucleoside diphosphate Kinase, phosphorylates histidine and protein histidine phosphatase (PHP) dephosphorylates histidine. It has been found that histone (H4), which is one of the most abundant proteins in eukaryotic cells, and which, along with the core histones (H2A, H2B, and H3), forms the proteinaceous spool around which DNA is packaged in chromatin, is phosphorylated on histidine, located on positions 18 and 75 of H4. It has also been found that H4 histidine Kinase activity is about 400 times higher in human hepatocellular carcinoma liver tissue as compared to normal liver tissue. Thus, H4 histidine Kinase activity is strongly correlated with liver growth. Further, it has been found that mutation of His-18 (to either Ala or Gln) profoundly perturbed chromosome silencing in yeast and that this had the biggest effect on any of H4 mutants in silencing the yeast.

Despite these discoveries, further understanding of histidine phosphorylation has been impeded because it is technically challenging to detect and isolate pHis proteins. To further complicate matters, histidine can be phosphorylated in vivo at either of the nitrogen atoms in the imidazole ring, giving rise to two isomers, 1-phosphohistidine (1-pHis) and 3-phosphohistidine (3-pHis). Both isomers have a phosphoramidate (P—N) bond, which thermodynamically is higher in energy ($\Delta G°$ of hydrolysis: about −12 to about −14 kcal/mole) than the phosphoester bond of phosphohydroxyamino acids, as in pSer, pThr or pTyr ($\Delta G°$ of hydrolysis: about −6.5 to about −9.5 kcal/mole). Under acidic conditions, pHis is rapidly hydrolyzed due to protonation of the imidazole ring. Although pHis is stable under basic conditions, the instability of pHis under acidic conditions severely hampers detection and isolation of the pHis using standard protocols. Indeed, the instability of pHis in acidic conditions has impeded the development of antibodies to molecules containing pHis. For example, no specific antibodies against pHis-containing proteins have been found since immunogens with pHis will be dephosphorylated in serum.

Moreover, to further complicate matters, even though chemical phosphorylation of protein and peptides can be selectively carried out on histidine residues, it is difficult to obtain the 1-pHis form region selectively, since 1-pHis isomerizes to the more thermodynamically stable 3-pHis under phosphorylation reaction conditions.

The present inventors, however, have found tools to investigate these problems. They have made pHis analogs which have been incorporated into peptides and proteins and have used these in the development of haptens and immunogens. The present inventors have prepared semi-synthetic pHis containing proteins and have generated pHis antibodies to further investigate the physiological functions of pHis.

SUMMARY OF THE INVENTION

The present invention is directed to a phosphoryltriazole of formula I:

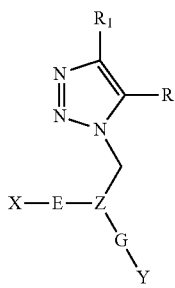

or salts thereof,
wherein X and Y are independently
—OR$_9$, —NR$_9$R$_{10}$, —SR$_9$, —COOR$_9$, —CONR$_9$R$_{10}$, NHJ, COQ or H;
Z is CH, N or Si R$_n$;
E and G are independently a chemical bond or a linker group selected from alkyl, alkenyl, alkynyl, cycloalkyl, cycloalkylalkyl, aryl, arylalkyl, cycloalkenyl, cycloalkenylalkyl, (CH$_2$)q wherein one of the methylene groups is replaced by O, (O—CH$_2$CH$_2$)n, heterocyclic or heterocyclicalkyl,
n is 1-100;
q is 1-6;
R$_9$ and R$_{10}$ are independently hydrogen, alkyl, alkenyl, alkynyl, cycloalkyl, cycloalkyl alkyl,
aryl, arylalkyl, heterocyclic or heterocyclic alkyl;
R$_{11}$ is H or alkyl and
J is an amino protecting group;
Q is an acid protecting group;
one of R$_1$ and R is

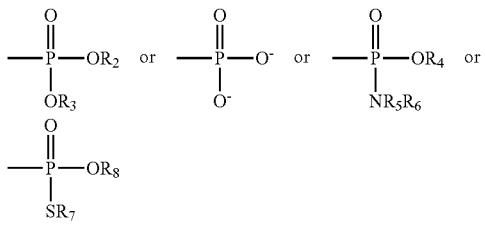

and the
other is hydrogen
R$_2$, R$_3$, R$_4$, R$_5$, R$_6$, R$_7$ and R$_8$ are independently H, alkyl, alkenyl, cycloalkyl, cycloalkylalkyl, aryl, arylalkyl, heterocyclic, heterocyclicalkyl, or a phosphate protecting group.
Another aspect of the present invention is directed to a hapten comprising the fragment of

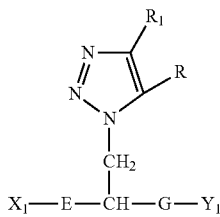

wherein R, R$_1$, E and G are as defined hereinabove, and X$_1$ and Y$_1$ are independently a chemical bond,

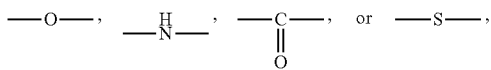

In another aspect, the hapten can be conjugated to carrier material to provide immunogens for antibody production and conjugates.

In still further aspects, the present invention provides an immunogen comprising a hapten of the present invention coupled to an antigenicity conferring carrier material. The carrier material may be, for example, a protein, a protein fragment, a synthetic polypeptide or a semi-synthetic polypeptide.

In a still further aspect, the present invention is directed to an isolated antibody raised against the immunogen of the present invention. This antibody recognizes pHis as well as the phosphoryltriazolyl compounds of the present invention, but does not recognize non-phosphorylated His or peptides which are not phosphorylated or amino acids which are not histidine which are phosphorylated or peptides which are phosphorylated on amino acid residues other than histidine and not on histidine.

In a still further aspect, the present invention comprises a conjugate comprising the hapten of the present invention covalently bonded to a labeling agent. For example, the labeling agent is selected from an enzyme, a luminescent substance, a radioactive substance or mixture thereof. In one embodiment, the labeling agent is an enzyme, such as a peroxidase, e.g., horseradish peroxidase. Alternatively or additionally, the luminescent substance may be a bioluminescent, chemiluminescent or fluorescent material.

In a further aspect, the present invention provides a process of preparing the antibodies, the process comprising the steps of immunizing an animal, such as a vertebrate animal, e.g., a mammal, by repeated administration of the immunogen of the present invention and collecting the resulting serum from the immunized animal and isolating the antibodies from the serum using techniques known to one of ordinary skill in the art. In another embodiment, the present process comprises exposing the immunogen of the present invention to a phage-display library expressing antibodies and isolating the phages and the antibodies that specifically bind to the immunogen using techniques known to one of ordinary skill in the art. In another aspect, the present invention relates to a process which comprises fixing these serum antibodies to a backing substrate, such as, for example, a solid support, e.g., polypeptide. The antibodies may be monoclonal or polyclonal. The antibodies of the present invention do not recognize non-phosphorylated proteins or amino acids, but do recognize phosphorylated histidine residues, but not other phosphorylated amino acids.

In a further aspect, the invention comprises a method of detecting a phosphorylated histidine in a biological sample comprising contacting the sample with the conjugate of the present invention or a mixture thereof and with antibodies of the present invention or a mixture thereof, detecting or determining bound conjugate and deducing from a calibration curve the presence or amount of phosphopolypeptide containing a phosphorylated histidine in the biological sample. The biological sample is usually a solution, e.g., serum or urine.

The present invention includes a kit for detecting phosphorylated polypeptides comprised of at least one phosphorylated histidine residue in a biological sample, the kit including the one or more the haptens and the antibodies of the present invention or a mixture thereof. The kit may optionally include instructions for use of haptens and the antibodies for detecting and or determining the presence of phosphorylated polypeptides comprised of at least one phosphorylated histidine residue.

BRIEF DESCRIPTION OF THE DRAWINGS

FIG. 4A provides the HPLC retention time and FIG. 4B provides the ESI MS of peptide 21.

DEFINITIONS

Figure 1:
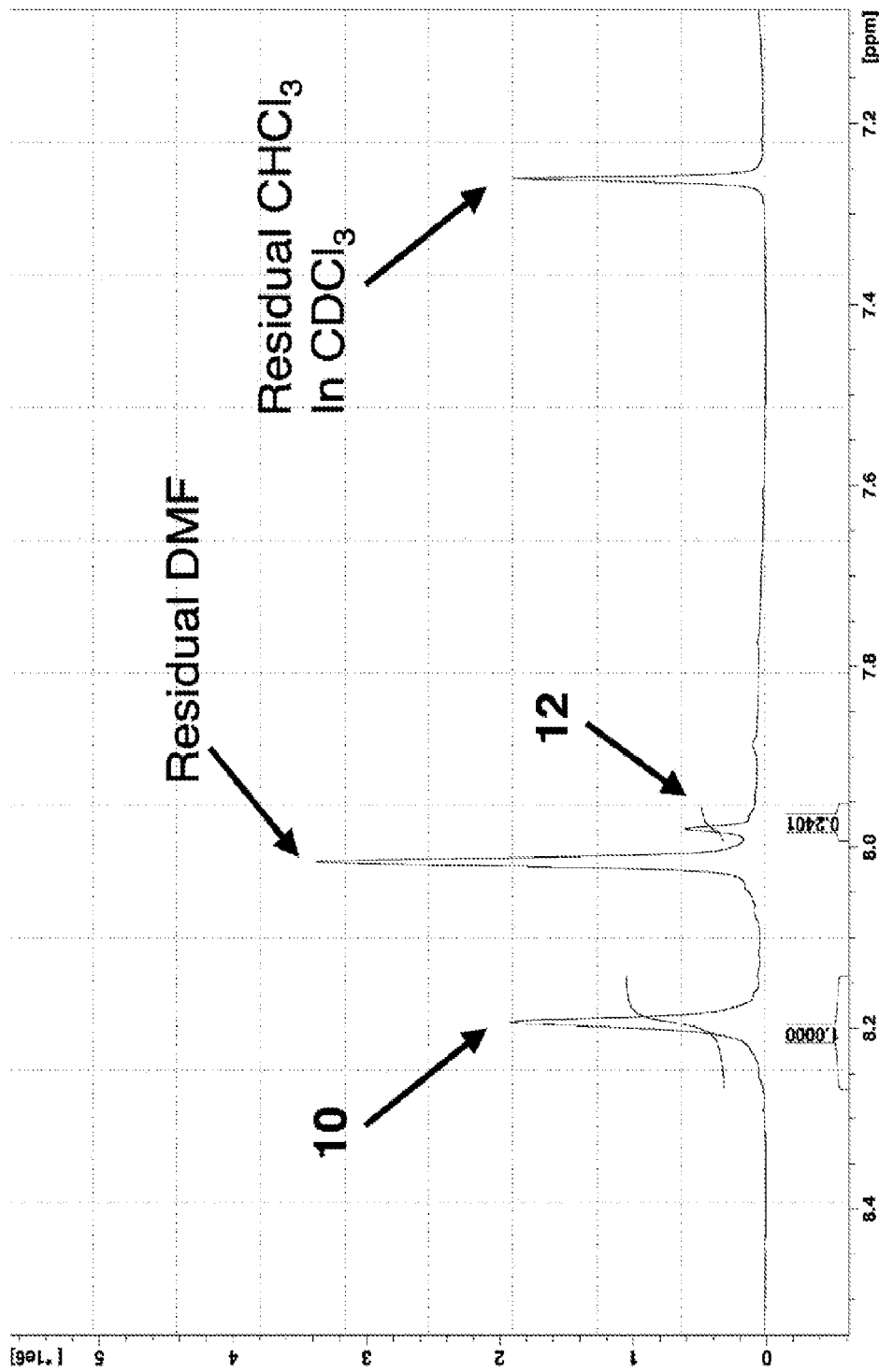
FIG. 1 is the $^1$H NMR of crude product mixture from the thermal cyclo addition between Boc-azidoalanine and diethyl ethynylphosphonate.

Throughout the present specification the following definitions are to be understood.

As used herein, the term "alkyl", when used alone or in combination with other groups, refers to an alkyl group containing 1-15 carbon atoms. The alkyl group may be straight chained or branched. The alkyl groups may be a lower alkyl group containing 1-6 carbon atoms. Examples of alkyl groups include methyl, ethyl, n-propyl, isopropyl, n-butyl, isobutyl, sec-butyl, t-butyl, n-pentyl, isopentyl, neopentyl, 2-methylpentyl, n-hexyl, 2,2-dimethylpentyl, 3-methylpentyl, 2,2-dimethylbutyl, 2,3-dimethylbutyl, heptyl, octyl, nonyl, decyl and the like.

The term "alkoxy", when used alone or in combination with other groups, refers to a terminal oxy containing alkyl group, as defined above such as methoxy, ethoxy, propoxy, isopropoxy and the like.

The term "cycloalkyl", when used alone or in combination with other groups, refers to the cyclic analog of an alkyl group, as defined herein, which contains 3 to 10 ring carbon atoms. It may be monocyclic or bicyclic or tricyclic. The cycloalkyl groups contain no ring saturation, although as described below, they may have unsaturated substituents. The cycloalkyl groups include cycloalkyl groups containing 3, 4, 5 and 6 ring carbon atoms. Examples of cycloalkyl include cyclopropyl, cyclobutyl, cyclopentyl, cyclohexyl, cycloheptyl, cyclooctyl, cyclodecyl, adamantyl and the like.

The terms "alkenyl" and "alkynyl", when used alone or in combination with other groups, refer to mono or poly unsaturated aliphatic hydrocarbon radicals containing from two to 15 carbon atoms, containing at least one double or triple bond, respectively. "Alkenyl" and "alkynyl" refer to both branched and unbranched alkenyl and alkynyl groups, respectively. The alkenyl and alkynyl groups include straight chained alkenyl or alkynyl groups containing from two to eight carbon atoms and branched alkenyl or alkynyl groups containing from five to 10 carbon atoms. The alkenyl and alkynyl groups also include alkenyl and alkynyl groups containing from two to six carbon atoms and branched alkenyl and alkynyl groups containing from 5 to eight carbon atoms. Examples of alkenyl groups include ethenyl, 2-propenyl, 1-propenyl, 2-methyl-1-propenyl, 1-butenyl, 2-butenyl, 1-pentenyl, 2-pentenyl, 3-pentenyl, allyl, 1, 3-butadienyl, 1,3-dipentenyl, 1,4 dipentenyl, 1-hexenyl, 1,3-hexenyl, 1,4-hexenyl, 1,3,5-trihexenyl, 2,4-dihexenyl, and the like. Examples of alkynyl include ethynyl, 1-propynyl, 2-propynyl, 1 butynyl, 2-butynyl, 2-methyl-1-butynyl, 1-pentynyl, 2-pentynyl, 3-pentynyl, 3-methyl-1-pentynyl, 2-methyl-1-pentynyl, 1-hexynyl, 2-hexynyl, 3-hexynyl, and the like. The alkenyl and alkynyl groups contain at least one 1 double bond or 1 triple bond, respectively. In another embodiment, they each may contain up to 4 carbon-carbon multiple bonds, for example, 1, 2, 3, 4, double bonds or triple bonds, respectively. The double bonds in the alkenyl groups may be conjugated, as in 1,3-butadienyl, or non-conjugated, as in 1,4-di pentenyl.

The term "cycloalkenyl", when used alone or in combination with other groups refers to the cyclic analog of an alkenyl group containing from 3 to 10 carbon atoms. The cycloalkenyl group contains from 3 to 10 ring carbon atoms. They may be monocyclic or bicyclic. They must contain at least one carbon-carbon double bond in the ring, and may contain more than 1 carbon-carbon double bond in the ring. In an embodiment, they contain up to 3 carbon-carbon double bonds in the ring. Thus the term cycloalkenyl include cycloalkenyl containing from three to eight ring carbon atoms. They also include cycloalkenyl containing 3, 4, 5 or 6 ring carbon atoms. It may be monocyclic or bicyclic.

The term "cycloalkyl alkyl", when used alone or in combination with other groups, refers to alkyl group, as defined hereinabove, substituted with an cycloalkyl group, as defined hereinabove wherein the cycloalkyl group is at the terminal end. Examples include cyclopentylmethyl, cyclohexylethyl and the like. Similarly, the term "cycloalkenylalkyl", when used alone or in combination with other groups, refers to an alkyl group substituted at the terminal position with cycloalkenyl, as defined herein.

The alkyl, alkenyl, alkynyl, cycloalkyl, cycloalkenyl, cycloalkylalkyl, cycloalkenylalkyl and alkoxy groups described hereinabove may be unsubstituted or substituted with one or more substituents selected from alkyl containing 1-6 carbon atoms, hydroxy, halo, including partially or fully halogenated, amino, cyano, nitro alkoxy containing 1-6 carbon atoms, alkyl amino, dialkylamino and the like.

The term "aryl", when used alone or in combination with other groups, refers to an aromatic hydrocarbon containing 6 to 14 ring carbon atoms. It includes aromatic rings fused to non-aromatic rings, as long as one of the fused ring is an aromatic hydrocarbon. Examples include phenyl and naphthyl. It may be unsubstituted or substituted, such as partially or fully halogenated, alkyl, hydroxyl; nitro; —COOH; —CO(lower alkoxy); —CO(lower alkyl); amino; alkylamino; dialkylamino; alkoxy; —NCOH; —NCO(lower alkyl); NSO$_2$-Ph(halo)$_{0-3}$, Phenyl, —O-Ph; naphthyl; —O-naphthyl. In an embodiment, aryl is unsubstituted phenyl or phenyl with at least one of the substituents described hereinabove.

The term "halo" refers to a halogen radical selected from fluoro, chloro, bromo or iodo.

The term "heterocyclic" when used alone or in combination with other groups refers to a 5-8 membered (for example, 5 or 6 membered) monocyclic or 8-11 membered bicyclic heterocyclic radical which may be either saturated or unsaturated, aromatic or non-aromatic, and which may be optionally benzo- or pyridofused if monocyclic, containing at least one ring heteroatom. Each heterocycle consists of carbon atoms and from 1 to 4 ring heteroatoms selected from the group consisting of nitrogen, oxygen and sulfur. As used herein, "nitrogen" and "sulfur" include any oxidized form of nitrogen and sulfur and the quaternized form of any basic nitrogen. Preferred heterocycles include, for example, benzimidazolyl, furazanyl; imidazolyl, imidazolinoyl, quinolyl, isoquinolyl, indolyl, oxazolyl, pyridyl, pyrrolyl, pyrrolinyl, pyrazolyl, pyrazinyl, pyrimidinyl, pyridazinyl, quinoxolyl, piperidinyl, morpholinyl, thiamorpholinyl, furyl, thienyl, triazolyl, thiazolyl, beta-carbolinyl, tetrazolyl, thiazolidinyl, benzofuranoyl, thiamorpholinyl sulfone, benzoxazolyl, oxopiperidinyl, oxopyrrolidinyl, oxoazepinyl, azepinyl, isoxazolyl, tetrahydropyranyl, tetrahydrofuranyl, thiadiazoyl, benzodioxolyl, tetrahydrothiophenyl and sulfolanyl, and the like. In an embodiment, the heterocycles o are imidazolyl, pyridyl, pyrrolyl, pyrazolyl, piperidinyl, morpholinyl, furyl, thienyl, thiazolyl and the benzo- and pyrido-fused derivatives thereof.

"Heterocyclyl" refers to unsubstituted heterocycle radicals as defined hereinabove, those radicals that are partially or fully halogenated and those radicals substituted with alkyl; hydroxyl; nitro; —COOH; —CO(lower alkoxy); —CO(lower alkyl); amino; alkylamino; dialkylamino; alkoxy; —NCOH; —NCO(lower alkyl); —NSO$_2$-Ph (halo)$_{0-3}$, Ph; O-Ph; naphthyl; —O-naphthyl; pyrrolyl; pyrrolyl substituted with lower alkyl; pyridyl; pyridinyl; pyrazinyl; pyrimidinyl and pyridazinyl, and the like.

The term "lower", used in conjunction with other terms (e.g., "alkyl", "alkoxy" and the like), refers to a radical containing from one to six, preferably from one to five and more preferably, from one to four carbon atoms. The "lower alkyl" group may be a branched or unbranched alkyl radical containing from one to six carbon atoms.

As described hereinabove, E and G include, in their definition, lower alkyl wherein one of the carbon atoms is replaced by O. This refers to a (CH$_2$)p group where p is 1-6 wherein one of the CH$_2$ groups is replaced with an oxygen atom.

The phosphate protecting groups are protecting groups for the phosphate groups known in the art. Examples are described in Wuts and Green, "Protective groups in Organic Synthesis", 4$^{th}$ Edition, Wiley-Interscience, 2006, NY. ISBN 978-0471697541, Chapter 9, pg 665-700, the contents of which are incorporated herein by reference. Examples include alkyl phosphates, e.g., methyl, ethyl, 4-N-trifluoroacetylaminobutyl, isopropyl, cyclohexyl, t-butyl, 1-adamantyl, allyl, 2-trimethylsilylprop-2-enyl, 3-pivaloyloxy-1,3-dihydroxy propyl, and the like; 2-substituted ethyl phosphates, such as 2-cyanoethyl, 2-cyano-1,1-dimethylethyl; 4-cyano-2-butenyl, Ar NH CO CH$_2$CH$_2$— wherein Ar is as defined above, 2-(methyl-diphenylsilyl) ethyl, 2-(trimethylsilyl) ethyl, 2-(triphenyl silyl) ethyl, 2-(S-acetythio) ethyl, 2-4-nitrophenyl)ethyl, 2-(2'-pyridyl)ethyl, 2-(4'-pyridyl) ethyl, 2-(3-aryl pyrimidin-2-yl) ethyl, wherein aryl is as defined hereinabove, 2-(phenylthio) ethyl, 2-(4'-nitrophenyl) thioethyl, 2-(4'-triphenylmethylphenylthio) ethyl, 2-[2'-(monomethoxytrityl(oxy)ethylthio]ethyl, HOCH$_2$CH$_2$SS (CH$_2$)$_2$, 2-(t-butylsulfonyl) ethyl, 2-(phenylsulfonyl) ethyl, 2-(Benzyl sulfonyl) ethyl, and the like; haloethyl phosphates, such as 2,2,2-trichloroethyl, 2,2,2-trichloro-1,1-dimethylethyl, 2,2 2-tribromoethyl, 2,3-dibromopropyl, 2,2,2-trifluoroethyl, 1,1,1 3,3,3-hexafluoro-2-propyl, and the like; benzyl phosphates, including benzyl, o-nitrobenzyl, 4-nitrobenzyl, 2,4-dinitrobenzyl, 4-chlorobenzyl, 4-chloro-2-nitrobenzyl, 4-acyloxybenzyl, 1-oxido-4-methoxy-2-picolyl, fluorenyl-9-methyl, pyrenylmethyl, 2-(9,10-anthraquinolyl) methyl, 5-benzisoxazoylmethylene, diphenylmethyl, o-xylene, benzoin, 3',5' dimethoxybenzoin, 4-hydroxyphenacyl, 4-methoxyphenyl, and the like, phenyl phosphates, such as phenyl, 2-methylphenyl, 2-6-dimethylphenyl, 2-chlorophenyl, 4-chlorophenyl, 2,4-dichlorophenyl, 2,5-dichlorophenyl, 2,6-dichlorophenyl, 2-bromophenyl, 4-nitrophenyl, 3,5-nitrophenyl, 4-chloro-2-nitrophenyl, 2-chloro-4-triphenylmethylphenyl, 2-methoxy-5-nitrophenyl, 1,2-phenylene, 4-triphenylmethylaminophenyl, 4-benzylaminophenyl, 1-methyl-2-(2-hydroxyphenyl imidazole, 8-quinolyl, 5-chloro-8-quinolyl, thiophenyl, and the like; amidates, such as anilidate, 4-triphenylmethylanilidate, [N-(2-trityloxy)ethyl]anilidate, p-(N,N-dimethylanino)anilidate, p-Anisidate, 2,2'-diaminobiphenyl, N, N'-dimethyl-(R, R)-1,2-diaminocyclohexyl and morpholinyl and the like.

"Haptens" are partial or incomplete antigens. They are protein-free substances, mostly low molecular weight organic compounds, which are not capable of stimulating antibody formation, but which do react with antibodies. They are formed by coupling the hapten to a high molecular weight immunogenic carrier using conventional conjugate chemistry (as further explained below) and then injecting this coupled product, i.e., immunogen, into a human or animal subject. The hapten of this invention is as defined herein. An embodiment is a polypeptide containing

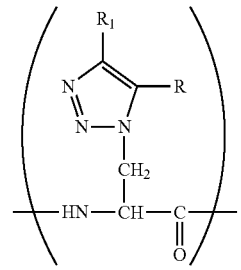

where R and R$_1$ are as defined herein.

The terms "immunogen" and "immunogenic" refer to substances capable of eliciting, producing, or generating an immune response in a living mammal.

The term "conjugate" refers to any substance formed from the joining together of two parts. Representative conjugates in accordance with the present invention include those formed by the joining together of a small molecule, such as the compound of formula I or a hapten of the present invention, as defined hereinabove, and a large molecule, such as a carrier or a polyamino acid or polyamine polymer, particularly a protein. In the conjugate, the small molecule may be joined at one or more active sites on the large molecule, directly or indirectly through a spacer or linking agent. The term conjugate includes the term immunogen.

As used herein, a "spacing group" or "spacer" refers to a portion of a chemical structure which connects two or more substructures such as haptens, carriers, immunogens, labels, or tracers through a CH$_2$ or a functional linking group. The atoms of a spacing group and the atoms of a chain within the spacing group are themselves connected by chemical bonds.

The term "linker" refers to a chemical moiety that connects a hapten to a carrier, immunogen, label, tracer or another linker Linkers may also be used to attach antibodies to labels or solid substrates. Linkers may be straight or branched, saturated or unsaturated carbon chains They may also include one or more heteroatoms within the chain or at the termini of the chains. By heteroatoms is meant atoms other than carbon which are chosen from the group consisting of oxygen, nitrogen, sulfur, phosphorus, boron and halogen. The use of a linker may or may not be advantageous or needed, depending on the specific hapten and carrier pairs. Methods and techniques for the attachment of a linker to an antibody are known in the art. For a good treatise on this subject, the reader is referred to *Bioconjugate Techniques*, G. Hermanson, Academic Press, 1996.

Among the spacers contemplated are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen, sulfur, phosphorus, boron and halogen. Spacing groups may also include cyclic or aromatic groups as part of the chain or as a substitution on one of the atoms in the chain.

The number of atoms in the spacing group is determined by counting the atoms other than hydrogen. More specifically, the number of atoms in a chain within a spacing group is determined by counting the number of atoms other than hydrogen along the shortest route between the substructures being connected. A functional linking group may be used to activate, e.g., provide an available functional site on a hapten or spacing group for synthesizing a conjugate of a hapten with a label or carrier or polyamine polymer. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. Various linking agents are well known in the art; see, for example, Cautrecasas, *J. Biol. Chem.*, (1970) 245:3059, and Cross-Linking Reagents, Technical Handbook by Pierce Company (Rockford, Ill.)

An "immunogenic carrier," as the term is used herein, is an immunogenic substance, commonly a polypeptide or protein, that can join with a hapten, in this case or the derivatives herein described, thereby enabling these hapten derivatives to induce an immune response and elicit the production of antibodies that can bind specifically with these haptens. Among the immunogenic carrier substances are included proteins, glycoproteins, complex polyamino-polysaccharides, and nucleic acids that are recognized as foreign and thereby elicit an immunologic response from the host. The polyamino-polysaccharides may be prepared from polysaccharides using any of the conventional means known for this preparation. Also various protein types may be employed as a poly (amino acid) immunogenic carrier. These types include albumins, serum proteins, lipoproteins, and the like. Illustrative proteins include bovine serum albumin (BSA), bovine gamma-globulin (BgG), keyhole limpet hemocyanin (KLH), egg ovalbumin, bovine thyroglobulin (BTG), and the like. Alternatively, synthetic poly (amino acids), polymerized protein or cross-linked protein may be utilized.

Immunogenic carriers can also include poly amino-polysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide also contains polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns and not more than about 100 microns and usually about 0.05 microns to about 10 microns in diameter. The particle can be organic or inorganic, swellable or non-swellable, porous or non-porous, optimally of a density approximating water, generally from about 0.7 to about 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses, and the like. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 500 daltons in molecular weight, having no upper molecular weight limit, normally being less than 10,000,000 and usually not more than about 600,000 daltons. There will usually be different ranges, depending on whether an immunogenic carrier or an enzyme is involved.

"peptide" is any compound formed by the linkage of two or more amino acids by amide (peptide) bonds, usually a polymer of alpha-amino acids in which the alpha-amino group of each amino acid residue (except the $NH_2$ terminus) is linked to the alpha-carboxyl group of the next residue in a linear chain. The terms peptide, polypeptide and poly (amino acid) are used synonymously herein to refer to this class of compounds without restriction as to size, unless indicated to the contrary. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments such as fab, fab' and (fab')$_2$, and the like, and application products containing these materials such as chimeric antibody, or humanized antibody, and the like.

In the present specification, antibody specificity refers to the property of an antibody which enables it to recognize, react, or bind to some particular antigenic determinants and not others. Specificity is dependent on chemical composition, physical forces, and molecular structure at the binding site.

The term "derivative" refers to a chemical compound or molecule made from a parent compound by one or more chemical reactions. The term "residue" in reference to the phosphoryltriazoly compound of Formula I refers to the phosphoryltriazolyl compound of the formula

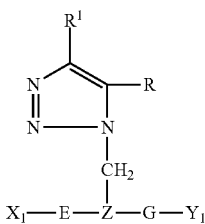

wherein $R^1$, $R^2Z$, E and G are as defined hereinabove and $X_1$ and $Y_1$ are independently NH, O, acyl group

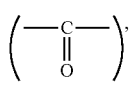

or —S—. For example, as explained below, in one embodiment, it has the structure

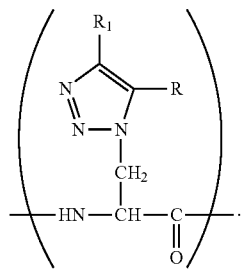

The term "amino acid residue" refers to the amino acid without the hydrogen on the amino group on the amino end and the OH group on the carboxyl at the carboxy end of the amino acid.

The term "carrier" refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to a terminal functional group in the haptens of the present invention.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for immunogens of the present invention, ligands of the analyte and calibration and control materials. The reagents may remain in liquid form or may be lyophilized.

The phrase "calibration and control materials" refers to any standard or reference material containing a known amount of a compound to be measured. The concentration of compound is calculated by comparing the results obtained for the unknown specimen with the results obtained for the standard. This is commonly done by constructing a calibration curve.

Test sample", as used herein, refers to a sample to be tested. The test sample is typically in liquid form. The test sample is typically a biological sample.

The term "biological sample" includes, but is not limited to, any quantity of a substance from a living organism or formerly living organism. Such living organisms include, but are not limited to, humans, mice, monkeys, rats, rabbits, horses, and other animals, and plants, bacteria, or fungi, and the like. Such substances include, but are not limited to, blood, serum, plasma, urine, cells, organs, tissues, bone, bone marrow, lymph, lymph nodes, synovial tissue, chondrocytes, synovial macrophages, endothelial cells, and skin, and the like.

DETAILED DESCRIPTION OF THE INVENTION

In an embodiment, the present invention is directed to phosphoryltriazole compounds of Formula I

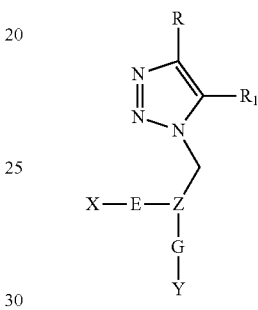

or pharmaceutically acceptable salts thereof wherein $R_1$, R, Z, E, X, G and Y are as defined hereinabove.

In an embodiment, Z is CH.

In another embodiment, E and G are independently a chemical bond, alkyl, alkenyl, cycloalkyl, cycloalkylalkyl, aryl, or arylalkyl. In another embodiment, E and G are independently a chemical bond or alkylene group of the formula, $(CH_2)m$, wherein m is 1 or 2 or $(CH_2O)m$. In another embodiment E and G are both chemical bonds. In still another embodiment Z is CH and E and G are independently chemical bonds or $(CH_2)m$ and in another embodiment E and G are both chemical bonds.

In an embodiment X and Y are independently $NR_9R_{10}$, $OR_9$, $COOR_9$, or lower alkyl which is unsubstituted or substituted with at least one halide, hydroxy, or leaving or group such as tosylate, mesylate or bresylate. In still another embodiment X and Y are independently $NR_9R_{10}$ and $COOR_9$. A further embodiment has X being $NH_2$ or NHB and Y being COOH or pharmaceutically acceptable salt thereof or COOP, where B is an amino protecting group or hydrogen and P is a carboxy protecting group or hydrogen, In a further embodiment, $R_2$, $R_3$, $R_4$, $R_7$ and $R_8$ are independently H, lower alkyl or benzyl or phosphate protecting group. In a further embodiment $R_2$, $R_3$, $R_4$, $R_7$ and $R_8$ have the aforesaid definitions and $R_5$ and $R_6$ are independently H or lower alkyl or cycloalkyl or aryl.

In another embodiment, one of R and $R_1$ is hydrogen and the other is

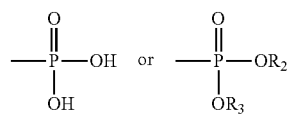

or salt thereof, wherein $R_2$ and $R_3$ are as defined hereinabove.

In a further embodiment the present invention is directed to a compound of the formula

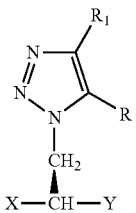

or salt thereof or zwitterion thereof
wherein R and $R^1$ are as defined hereinabove.

In another embodiment R is H and $R_1$ is

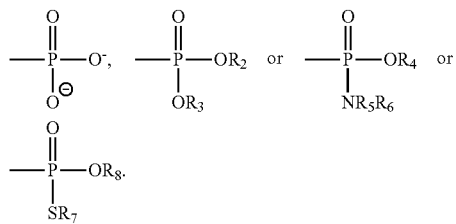

In another embodiment $R_1$ is H and R is

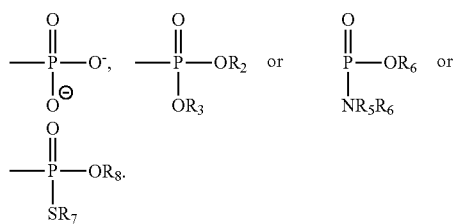

In another embodiment, one of R and $R_1$ is hydrogen and the other is

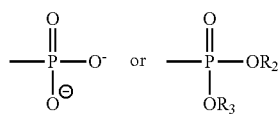

As defined herein, amino protecting groups are protecting groups known in the art. These protecting groups are described in a book entitled "Protecting Groups in Organic Synthesis" by Theodora Greene, John Wiley and Sons, NY, NY, 1982, the contents of which are incorporated herein, especially pages 223-287, which relate to the protection of amino groups. Examples of amino protecting groups include 9-fluorenylmethyoxy carbonyl (FMOC), 2-chloro-1-indanyl methoxy carbonyl (CLIMOC), benz-[f]-indene-3-methyl-oxycarbonyl (BIMOC), 2-(t-butyl sulfonyl)-2-propenyloxy-carbonyl (Bspoc), benzothiophene sulfone-2-methoxycarbonyl (Bsmoc), t-butyloxycarbonyl (BOC), t-amyloxycarbonyl (Aoc), beta-trimethylethyloxycarbonyl (TEOC), adamantyloxycarbonyl (Adoc), 1-methyl-cyclobutyloxycarbonyl (Mcb), 2-(p-biphenylyl)propyl-2-oxycarbonyl (Bpoc), 2-(p-phenylazophenyl)propyl-2-oxycarbonyl (Azoc), 2,2-dimethyl-3,5-dimethyloxybenzyloxycarbonyl (Ddz), 2-phenylpropyl-2-oxycarbonyl (Poc), benzyloxycarbonyl (Cbz), p-toluenesulfonyl aminocarbonyl (Tac), o-nitrophenylsulfenyl (Nps), dithiasuccinoyl (Dts), phthaloyl, piperidinooxycarbonyl, formyl, trifluoroacetyl and the like. Carboxylic acid protecting groups are known in the art. They include esters, especially, benzyl, methyl and ethyl esters. Examples of protecting groups for carboxylic acids are described in a book entitled "Protecting Groups in Organic Synthesis" by Theodore Greene, John Wiley & Sons, NY, NY, 1982, the contents of which are incorporated herein by reference. Examples include lower alkyl, aryl, aryl lower alkyl, lowercycloalkyl, and lower alkenyl groups such as methyl, methoxy-methyl, methyl-thiomethyl, tetrahydropyranyl, tetrahydrofuranyl, methoxyethoxymethyl, benzyloxymethyl, phenacyl, p-bromophenacyl, α-methylphenacyl, p-methoxyphenacyl, diacylmethyl, N-phthalimodomethyl, ethyl, 2,2,2-trichloroethyl, 2-haloethyl, omega-chlorolower alkyl, 2-(trimethylsilyl) ethyl, 2-methylthioethyl, 2-p-(nitrophenylsulfenyl) ethyl, 2-(p-toluenesulfonyl) ethyl, 1-methyl-1-phenylethyl, t-butyl, cyclopentyl, cyclohexyl, allyl, cinnamyl, phenyl, p-methyl thiophenyl, benzyl, triphenylmethyl, diphenylmethyl, Bis (o-nitrophenyl) methyl, 9-anthrylmethyl, 2-(9,10-dioxo)-anthrylmethyl, 5-dibenzsuberyl, 2,4,6-trimethylbenzyl, p-bromobenzyl, o-nitrobenzyl, p-nitro benzyl, p-methoxybenzyl, piperonyl, 4-picolyl, trimethylsilyl, triethylsilyl, triethylsilyl, t-butyldimethylsilyl, i-propyldimethylsilyl, phenyldimethyl-silyl, N-hydroxypiperidinyl, N-hydroxysuccinimide N-hydroxyphthalimide, N-hydroxy-benzotriazole, o-acyloxime, 2,4-dinitrophenylsulfenyl, triethylstannyl tributylstannyl esters and the like.

When Z is CH, the compound of Formula I contains an asymmetric carbon and can exist in two enantiomeric states. It may exist in either the L or D stereochemistry at the carbon atom at Z. Mixtures of the L and D isomers are contemplated by the present invention, including racemic mixtures thereof. In an embodiment, the compound of Formula I contains substantially the L-isomer of formula I'

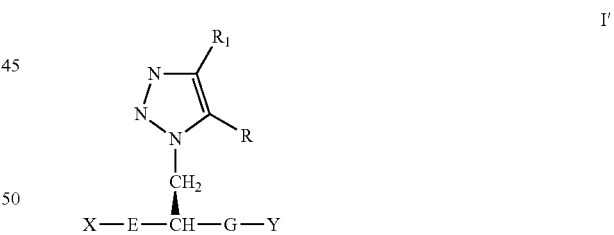

or salts thereof
wherein X, E, G, Y, R and $R_1$ are as defined herein.
When G and E are chemical bonds, this become

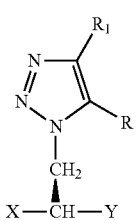

In another embodiment, X is

and Y is NB so that the compounds of Formula I becomes

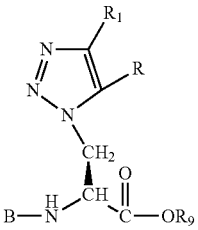

or salt thereof or zwitterion thereof, wherein R and $R_1$, $R_9$ are as defined hereinabove, and B is an amino protecting group or Hydrogen and wherein it is in present in substantially the L-isomer. By "substantially the L isomer", it is meant that it is substantially enantiomerically pure containing at least about 80% of L isomer. In one embodiment, it contains at least about 90% of L-isomer and in another embodiment, more than about 95% L-isomer.

The compound of Formula I described above is prepared by metal-catalyzed cycloaddition reactions. For example, an embodiment of Formula I, the Formula I''', has the formula:

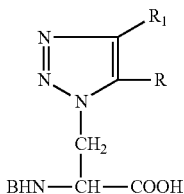

It is prepared from the reaction between an azidoalkane derivative of Formula II

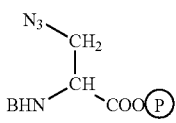

and the alkyne of Formula IV

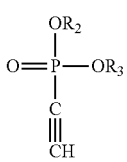

under Huisgen cycloaddition reaction conditions. In this embodiment B, $R_2$, $R_3$ are as defined hereinabove and X is $COOR_9$, wherein $R_9$ is as defined hereinabove. The reaction is effected in an inert solvent in which the reactants are soluble. The reaction is conducted at a temperature ranging from about room temperature up to and including the boiling point of the solvent. The reaction is run for sufficient time for the cycloaddition to occur. In some embodiments, it may be necessary to protect the carboxylic acid functionality with a protecting group known in the art. Again, various protecting groups may be utilized, and examples thereof are listed in the book entitled, "Protecting Groups in Organic Synthesis", by Theodora W. Greene, referred to hereinabove, especially Pages 152-192 thereof, the contents of which are incorporated by reference. Examples of protecting groups for the carboxyl group include tetrahydrofuryl and tetrahydropyranyl esters, and, esters, such as triphenylmethyl ester, t-butyl ester, methyl ester, benzyl ester, and the like.

In the following scheme, $R_1$ is H. The compound of Formula I''' is prepared by reacting an azido-alanine of Formula II with an alkyne of Formula III

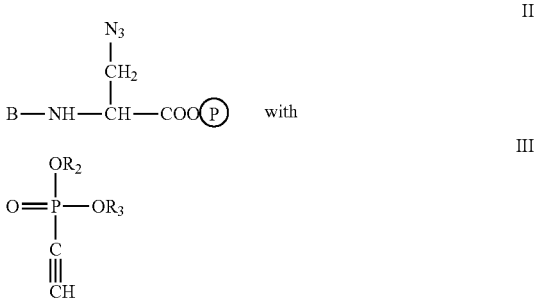

wherein

Ⓟ is an acid protecting group or hydrogen and B is an amino protecting group or hydrogen and $R_2$ and $R_3$ are as defined above under Husigen cycloaddition reaction conditions in the presence of an Ru (II) catalyst. The reaction is conducted in an inert solvent that dissolves the reactants, such as benzene, toluene, ethylbenzene and the like. In one embodiment, the ruthenium catalyst is rutheneacylcyclopentene. In another embodiment, the ruthenium catalyst is CpRu (COD) Q wherein Q is a halide, such as Br, F, Cl, or I and Cp is ruthenacylcyclopentene. In an embodiment, X is chloride. The reaction may be conducted in the presence of a carboxylic acid protecting group, such as benzyl, for example. The cycloaddition reaction is conducted at a temperature ranging from and including room temperature up to and including the boiling point of the solvent. After the cycloaddition reaction is completed, if an acid protecting group is present, it is removed to afford a compound of Formula I where $R_1$ is hydrogen.

When R is hydrogen, the compound of Formula I''' becomes

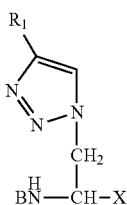

and it is prepared by reacting an azidoalanine compound of formula II

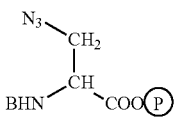   IV with an alkyne of the formula

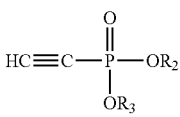   III in the presence of a copper catalyst, such as a cuprous halide, for example, cuprous iodide under Husigen cycloaddition reactions conditions to form the compound of Formula I. The reaction is effected in an inert solvent in which the reactants are soluble at a temperature ranging from about room temperature to about boiling point of the solvent for a time sufficient for the cycloaddition to take place. In these reactions, $R_1$ is

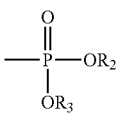

phosphonate group which can be converted to the other group of $R_1$ by techniques known in the art.

From these compounds, of Formula I''' other compounds of Formula I can be prepared by techniques known in the art. For example, by protecting the amino group in Formula I''', other functional groups on the left side of Formula I can be made. For instance, esters can be prepared from the carboxylic acid by reacting the carboxylic acid with an alcohol in the presence of acid such as p-toluenesulfonic acid, under ester forming conditions. Alternatively, the carboxylic acid can be converted to an acid chloride which is then reacted with an alcohol under ester forming conditions to form an ester. Alternatively, the ether functionality (e.g., alkoxy) can be prepared from the corresponding alcohol which is prepared by reducing the carboxyl group with a reducing agent known in the art, such as lithium aluminum hydride and by reacting the product with an alkyl halide, for example, in the presence of base. The amino functionality can be prepared from the carboxylic acid by converting the carboxylic acid into an amide by reacting the acid chloride with ammonia and then heating the amide under Hoffman degradation conditions to form an amine at the α-carbon. The Alkyl, alkenyl, alkynyl, cycloalkyl, cycloalkylalkyl, cycloalkenyl, cycloalkenylalkyl, aryl, aryl alkyl heterocyclic and heterocyclic alkyl substituents of E and X can be added to the molecule by reducing the carboxylic acid with lithium aluminum halide or other reducing agent known in the art to form an alcohol and converting the alcohol to a halide by techniques known in the art, such as reacting with Hydrochloride acid and then reacting the product with $R_2"CuLi$ under Gilman reaction conditions to form a carbon-carbon bond where R" is an allyl, alkenyl, alkynyl, cycloalkyl, cycloalkylalkyl, cycloalkenyl, cycloalkenylalkyl, aryl, arylalkyl, heterocyclic or heterocyclic alkyl.

On the other side of the molecule, the carboxy group of Y is protected with an acid protecting group, and the amino group is reacted. For example, it is reacted with alkyl halide to form a quaternary ammonium salt and then reacting the product thereof with base, such as KOH, under Hoffman elimination reaction conditions to form a carbon-carbon double bond. The carbon double bond can be reacted with HBr in the presence of peroxide to form a terminal bromide which in turn reacts with additional base (e.g. KOH) to form a terminal OH compound. This in turn can react with an alkyl halide in the presence of further base to form an ether under ether forming conditions. Moreover the alcohol can be oxidized by an oxidizing agent known in the art, such as $KMnO_4$, in the presence of acid to form a carboxylic acid. The resulting carboxylic acid can undergo the reactions discussed in the previous paragraph. For example, the carboxylic acid can then be converted to an acid chloride and react with an alcohol to form an ester under ester forming conditions. The halide described hereinabove can react with $R_2"CuL_1$ to form carbon bond wherein R" is defined above.

As shown by these sample reactions, it is possible to obtain various functional groups on both side of the Z moiety by techniques known to one of skill in the art. Thus, it is possible to convert both ends or one end of the molecule to the various groups contemplated by XE and GY.

In all of the reaction syntheses described hereinabove, it is understood that if the reactant contains functionalities thereon which are reactive under the reaction conditions, then before effecting the reaction, those functional groups are protected by protecting groups known in the art. At the end of the reaction or at the end of the overall synthesis, these protecting groups can be removed.

The reactions described herein are generally performed in solvents which solubilize the reactants and are conducted under temperatures and conditions sufficient to effect the reaction.

The compounds of Formula I are not in and of themselves immunogenic. They, however, can be conjugated to carrier material which will elicit an immunogen response when administered to a host animal. In an embodiment, it has a functional group thereon which is reactive with an antibody conferring carrier material. For example, it may be conjugated via the functional groups in E and G, or the functional groups on X and Y to an antibody conferring carrier material or to a linking group that in itself can conjugate to the antibody conferring carrier material. This is effected by techniques known to one of ordinary skill in the art.

Thus, an aspect of the present invention is directed to a hapten of the formula

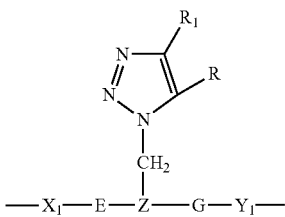

where R, $R_1$, E and G are defined hereinabove and $X_1$ and $Y_1$ are independently a bond,

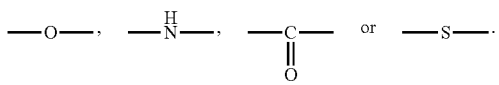

For example, in Formula I when $X_1$ is $NH_2$ and $Y_1$ is

the compound of Formula I can be bonded to other amino acids to form peptides.

When coupling the phosphorotriazole to form a peptide bond, it is understood that the phosphorotriazole of Formula I has at least either a free amino group or a free carboxy group or so that it could form a peptide bond. The peptide can bond to the antibody conferring material or linking group. Alternatively, the molecule of Formula I may be conjugated directly or through a linking group to an antibody conferring carrier material.

As described hereinabove, an embodiment of the present invention has the formula

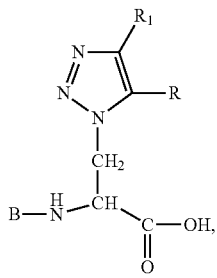

wherein B is hydrogen or base protecting group.

When the compound of Formula I is of the formula

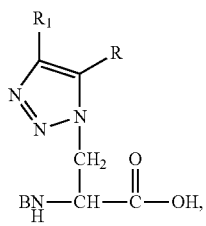

it is isosteric with phosphorylated histidine. Further, the electrostatics of the phosphonoltriazolylalanine mimic those of phosphorylated Histidine. In particular, the phosphonate group of N-methyl-triazolylphosphonic acid is fully ionized at physiological pH ($pK_1$=2.3 and $pKA_2$=5.3), analogous to pHis. Further, as shown below, suitably protected 1-pTza and 3-pTza analogs of p-His, described herein, are fully compatible with solid phase peptide synthesis (SPPS).

As described hereinbelow, the present inventors are the first to isolate an antibody that selectively recognizes a phosphorylated histidine containing protein utilizing the phosphoryltriazolylalanine of the present invention. This is effected by utilizing haptens comprising the phosphoryltriazolyla compounds residue of the present invention. These haptens can be prepared synthetically by standard techniques. In one embodiment, the haptens are polypeptides containing at least one phosphoryltriazolylalanines of the present invention and containing at least about 8 amino acid residues. In an embodiment, the hapten is a compound of the formula:

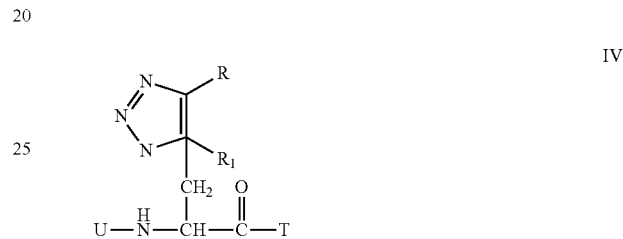

wherein T is OH or an amino acid residue of 1-15 amino acid residues and U is H or amino acid residue of 1-15 amino acid residues and $R_1$ and R are as defined hereinabove, wherein the amino acids are Gly, Ala, Val, Leu, Ile, Asp, Glu, Asn, Gln, Lys, His, Pro, Phe, Trp, Tyr, Ser, Thr, Met, Cys or Arg or

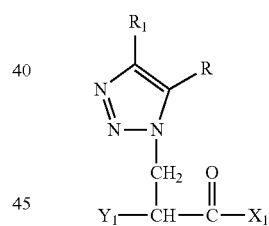

and $X_1$ is a bond or NH, and $Y_1$ is a bond or OH, wherein the sum of U and T ranges from 1 to about 100, i.e., contains from 1 to about 100 amino acid residues. In another embodiment, the present invention comprises the hapten of Formula IV, wherein the hapten is a polypeptide of 1 to about 200 amino acids.

These haptens of Formula IV be prepared using art-recognized techniques. For example, the hapten of Formula IV is prepared by standard peptide synthesis. In one embodiment, the hapten is prepared from the compounds of Formula I with E and G being chemical bonds, Y being COOH or acyl derivative and X being an amino group by reacting Formula I with peptides under peptide forming conditions, e.g., by liquid phase peptide synthesis. In another embodiment, the hapten of Formula IV is prepared from the compounds of Formula I with E and G being chemical bonds, Y being COOH or acyl derivative and X being an amino group by reacting Formula I with peptides under peptide forming conditions, e.g., by solid phase peptide synthesis, e.g., the Merrifield peptide synthesis or reverse Merrifield peptide synthesis. Although various haptens can be prepared, in an embodiment of the present invention, the haptens are based upon naturally occurring polypeptides whereby at least one of the histidines in the polypeptide is replaced by a p-Tza (phosphorylatedtriazolylalanie) of the present invention. It may be the full polypeptide or fraction thereof, wherein at least one of the histidine residues normally present is replaced by the phosphoryltriazaolyl alanine of the present invention. For example, by using solid phase peptide synthesis, histone H4 or fragments thereof wherein either the histidine at position 18 or at position 75 or both are replaced by the phosphoryltriazolylalanine residue of the present invention may be prepared. The following are examples of haptens of the present invention: that can be prepared using the peptide forming techniques described herein:

```
                                          (Seq ID #1)
Ac-Cys-Gly-Ala-Lys(Ac)-Arg-3-pTza-Arg-Lys-Val-Leu-
Arg-NH2-
(H4 pHis 18)

(Seq ID #2)
Ac-Cys-Gly-Ala-Lys-Arg-3-pTza-Arg-Lys(Me)-Val-Leu-
Arg-NH2
(H4 pHis 18)

(Seq ID #3)
Ac-Cys-Val-Thr-Tyr-Thr-Glu-3-pTza-Ala-Lys-Arg-
Lys-T hr-NH2
(H4 His 75)

(Seq ID #4)
Ac-Cys-Arg-Asn-Ile-Ile-3-pTza-Gly-Ser-Asp-Ser-
Val-NH2
(NDPK-A/B)

(Seq ID #5)
Ac-Cys-Gly-Ala-Lys(Ac)-Arg-1-pTza-Arg-Lys-Val-Leu-
Arg-NH2-
(H4 pHis 18)

(Seq ID #6)
Ac-Cys-Gly-Ala-Lys-Arg-1-pTza-Arg-Lys(Me)-Val-Leu-
Arg-NH2
(H4 pHis 18)

(Seq ID #7)
Ac-Cys-Val-Thr-Tyr-Thr-Glu-1-pTza-Ala-Lys-Arg-Lys-
T hr-NH2
(H4 His 75)

(Seq ID #8)
Ac-Cys-Arg-Asn-Ile-Ile-1-p-Tza-Gly-Ser-Asp-Ser-
Val-NH2
(NDPK-A/B)
```

Another embodiment of the present invention is directed to immunogens in which a hapten of the present invention is coupled to an antibody conferring carrier material. The haptens of the present invention are employed in the preparation of immunogens by coupling them to modified or non-modified antigenicity-conferring carrier materials to provide immunogens for antibody production and conjugates (tracers) using synthetic organic chemistry techniques.

The hapten may be bonded directly to the carrier material or indirectly through a linking group. Spacer groups may be added to the hapten or to the carrier. The hapten, on the one hand, may be linked to the carrier by a linker, which links one group on the carrier with another group on the hapten. A hapten can directly or indirectly (via a spacer or linker) be coupled to a carrier protein to form an immunogen such as hapten-enzyme conjugate. The hapten can also be linked to other non-enzymatic reporter groups such as a chromogen, a fluorescent compound, a phosphorescent compound or a chemiluminescent material, and the like. For example, in an embodiment of the present invention, the hapten is a polypeptide wherein the end groups thereon are functional groups, the amino group at one end and a carboxy group at the other end. The linkage may be through the carboxylic acid or phosphoric acid of the hapten and the alcohol if present, on the carrier to form an ester or through the carboxyl group of the hapten and amino group, if present, of the carrier to form an amide. However, if necessary, the carboxy group or the amino group may be further functionalized to form other bonds with the carrier molecule. For example, the carboxy group may be reduced to form an alcohol group by techniques known in the art and linked to the carboxyl group, if present, of the carrier to form an ester. Alternatively, the alcohol may be converted to a halide or other good leaving group, such as mesylate, tosylate, brosylate and reacted with other groups on the carrier by substitution reactions. In another embodiment, the side groups of the amino acid residues may react with functional groups on the carrier molecules. For example a sulfhydryl (mercaptan) can react with an olefin, halogen, or other alkylating agents to form thioethers. In another embodiment, a linking group which contains two functionalities, one reactive with the hapten to be linked thereto and one reactive with the carrier may be added to either the hapten or the carrier and react with a functional group on the carrier or hapten, respectively. Other bio-conjugation reactions can be effected as illustrated in the literature of conjugation chemistry, such as in the Bioconjugate Techniques book described hereinabove. Additionally, if the carrier has a ribose or adenine moiety thereon, it can be coupled to the haptens of the present invention via the functional groups in the ribose or the adenine moiety.

The carrier material typically is a protein, a protein fragment, a synthetic polypeptide or a semi-synthetic polypeptide. Illustrative examples of useful carrier materials are bovine serum albumin (BSA), egg ovalbumin, bovine gamma globulin, thyroxine binding globulin, keyhole limpet haemocyanin (KLH) and the like. Alternatively, synthetic poly(amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen.

Each hapten of the present invention can also be coupled to a labeling agent. For example, it may be coupled to an enzyme. Any common reporter enzyme (e.g., alkaline phosphatase or AP, and beta-galactosidase or beta-gal, horseradish peroxidase or HRP, and the like) can be use for preparation of hapten-enzyme conjugate. The hapten may be coupled to a substance having fluorescent properties or a radioactive label for the preparation of conjugates (or detection reagents) for use in the immunoassay. The fluorescent substance may be, for example, a monovalent residue or flouroescein or a derivative thereof.

In order to confirm that adequate conjugation of hapten to carrier material has been achieved prior to immunization, each immunogen is evaluated to verify that the hapten is conjugated to a carrier material. For example, the immunogen may be evaluated using matrix-assisted UV laser desorption ionization time of flight mass spectroscopy (MALDI-TOF-MS).

The immunogens obtained are then administered to hosts to elicit production of specific antibodies, i.e., polyclonal or monoclonal antibodies, which are then used to develop immunoassays for the detection and determination of p-His polypeptides in a biological sample. Each of the immunogens of the present invention is suitable for immunization to produce the antibodies described hereinbelow. For specific application, the hapten may be coupled to antibody, or biotin/avidin (or streptavidin), and the like. The antibody can be a monoclonal antibody or a polyclonal antibody.

The immunogen is administered to animals such as rabbits, mice, rats, chickens, sheep, goats, or cows, and the like by a series of injections according to techniques generally known in the art. An antibody, according to the present invention, is raised in response to an immunogen of the invention which is derived from a substantially purified hapten including optically pure hapten of the invention. Both polyclonal and monoclonal antibodies recognize specific epitopes on an immunogen, and, while typically polyclonal antibodies have been utilized in the present invention, both may be suitable. Polyclonal antibodies consist of a mixture of multiple antibodies, each recognizing a specific epitope, whereas monoclonal antibodies are produced by cells secreting a single antibody recognizing a specific epitope. Techniques for preparing polyclonal antibodies and monoclonal antibodies generally are well known in the art.

The antibodies of the present invention recognize the His and the pTza of the present invention or peptide containing same.

The antibodies do not recognize amino acids other than histidine which are phosphorylated, nor do they recognize peptides including polypeptides, which are not phosphorylated or are phosphorylated on amino acids other than histidine but not on histidine. As long as the peptide contains 1 histidine moiety that is phosphorylated, even if the other histidine moieties therein are not phosphorylated, the antibody will recognize the peptide.

Thus, even after separation of the antibodies, and the antibodies are isolated, to verify that the correct antibodies are collected non-phosphorylated histidine or the peptide containing non-phosphorylated histidine is used. If the antibody does not recognize the non-phosphorylated histidine, then the antibody is kept. If it still recognizes the dephosphorylated His or peptide containing non-phosphorylated histidine, then the antibody is discarded.

The polyclonal antibodies are obtained by techniques known in the art. For example, in a method to generate anti sera and polyclonal antibodies, each immunogen is mixed with Freud's Adjuvant and the mixture injected into a host animal, such as rabbit, sheep, mouse, guinea pig or horse. Further, injections (boosts) are made and their serum is sampled for evaluation of the antibody titre. When the optimal titre has been attained, the host animal is bled to yield a suitable volume of specific anti serum. For many purposes, there is no requirement for purification, however, in other cases, such as where the antibody is immobilized on a solid support, purification steps can be taken to remove undesired material. The antibodies are then separated from the serum using techniques known in the art.

For example, monoclonal antibodies may be prepared by injecting animals, such as mice or rats, intraperitoneally, subcutaneously, intravenously, or in some other manner, with an antigen, namely an immunogen of the present invention linked to an immunogenic carrier, to elicit an immune response in the animals (namely, the production of antibodies which are specific for the antigen). Sera from the animals are drawn, and the sera are tested to determine the titer of antibody in the sera (to determine whether or not the animal elicited the desired immune response, and to what extent). Those animals in which the desired immune response has been produced are permitted to rest for approximately three weeks to three months for clearance of circulating antibodies. After this three weeks to three-month period of time, and approximately three days prior to the anticipated fusion of B-lymphocyte cells (cells which, upon stimulation by antigen, mature into plasma cells which synthesize antibody, and which are also referred to as B cells) with, for example, myeloma cells (tumor cells), a boost injection (intravenously preferred) of the antigen is administered to these animals. B-lymphocyte cells are then removed from the spleens and/or lymph nodes of these animals by standard procedures, and the B-lymphocyte cells are then fused with myeloma fusion partners according to standard procedures, such as those described in Ed Harlow and David Lane, "Antibodies, A Laboratory Manual," Cold Spring Harbor Laboratory, 1988, and in Kohler and Milstein, "Continuous Culture of Fused Cells Secreting Antibody of Predefined Specificity," *Nature*, 256, 495 (1975). The B-lymphocyte-myeloma fusions are then plated in multiwell tissue culture plates containing HT media, or other suitable media. The resulting cultures are fed with HT media, or other suitable media, and fetal bovine serum or calf serum on or about the fifth and seventh days after the fusion of the cells and then tested on or about the tenth day after the fusion for the presence of antibody which is specific for the antigen. Specific desirable hybrids are then cloned by limiting dilution (Hybrid cells are diluted in differing amounts of HT media, or other suitable media, and plated out in tissue culture plates in order to isolate a single desired clone.) Established clones are then retested for specificity to a broader panel of cross reactants.

The amount of the resulting monoclonal antibodies produced by a desired clone can then be scaled up to produce a sufficient quantity of antibody for purification in either: (1) tissue culture (by expanding the number of cells in tissue culture, or HT media); or (2) mice for ascites. The monoclonal antibodies can be scaled up in mice by injecting hybrid cells into the abdominal cavity of mice and allowing the cells to grow (usually for about 7 days). The ascites are harvested from the mice by sacrificing the mice, collecting the ascites fluid, and purifying the ascites fluid. BALB/c mice are the most common strain of laboratory mouse used for this process, and they can be obtained from any mouse vendor. Pristane should be injected into the mice to stimulate their immune systems to produce B and T cells (about two or three weeks before the hybrid cells are injected into the mice) which serve as a feeder layer for the clone cells that are injected into the mice. This is performed to provide a suitable environment in which the hybrid cells can grow.

The antibody fragments comprise a portion of an intact antibody, generally the antigen binding or variable region of the intact antibody. Examples of antibody fragments include Fab, Fab', F(ab')$_2$, and Fc fragments; diabodies; linear antibodies; single-chain antibody molecules; and multispecific antibodies formed from antibody fragments.

The antibody application derivatives and products are intended to include chimeric antibodies, humanized antibodies, genetically engineered or modified antibody sequences by site specific mutagenesis.

An additional method for selecting antibodies that specifically bind to the immunogens of the present invention or variant or fragment thereof is by phage display. In an embodiment, the antibodies prepared by the techniques hereinabove are collected. Human or murine immunoglobulin variable region gene combinatiorial libraries may be created in phage vectors, that can be screened to select the antibodies fragment (Fab, Fb, sFv or multimers thereof) that bind specifically to the immunogen of the present invention or variants or fragments thereof, but do not bind to the corresponding nonphosphorylated polypeptide using phase transfer techniques known to one of ordinary skill in the art. For example, a library containing a plurality of polynucleotide sequences encoding the antibody isolated hereinabove or variable region fragments can be prepared and inserted into the genome of a filamentous bacteriophage, such as M13 or variant thereof, in frame, with the sequence encoding a phage coat protein, for instance, gene III or gene VIII of M13 to create an M13 fusion protein with the antigen binding domain on the outside of the bacteriophage. The fusion protein may be a fusion of the coat protein with the light chain variable region domain and/or with the heavy chain variable region domain. A random population of variable region genes are cloned to give rise to a mixture of bacteriophages, that is a phase display library.

Phage that display an Ig fragment (e.g., an Ig V-region or Fab) that binds to the immunogen of the present invention may be selected by mixing the phage library with the immunogen of the present invention or a variant or a fragment thereof, or by contacting the phage library with a immunogen of the present invention immobilized on a solid matrix under conditions and for a time sufficient to allow binding. Unbound phage are removed by a wash, which typically may be a buffer containing salt (e.g., NaCl) at a low concentration, preferably with less than 100 mM NaCl, more preferably with less than 50 mM NaCl, most preferably with less than 10 mM NaCl, or, alternatively, a buffer containing no salt. Specifically bound phage is then eluted with a NaCl-containing buffer, for example, by increasing the salt concentration in a step-wise manner Typically, phage that bind the immunogen of the present invention with higher affinity will require higher salt concentrations to be released. Eluted phage may be propagated in an appropriate bacterial host, and generally, successive rounds of immunogen of the present invention binding and elution can be repeated to increase the yield of phage expressing immunogen of the present invention specific immunoglobulin.

Phage display techniques may also be used to select polypeptides, peptides or single chain antibodies that bind to immunogen of the present invention. The inserted DNA molecules may comprise randomly generated sequences, or may encode variants of a known peptide or polypeptide domain that specifically binds to the immunogen of the present invention, or variant or fragment thereof, as provided herein. Generally, the nucleic acid insert encodes a peptide of up to 60 amino acids, more preferably a peptide of 3 to 35 amino acids, and still more preferably a peptide of 6 to 20 amino acids. The peptide encoded by the inserted sequence is displayed on the surface of the bacteriophage. Phage expressing a binding domain for the immunogen of the present invention may be selected on the basis of specific binding to an immobilized immunogen of the present invention as described above. As provided herein, well-known recombinant genetic techniques may be used to construct fusion proteins containing the fragment thereof. For example, a polypeptide may be generated that comprises a tandem array of two or more similar or dissimilar affinity selected immunogens of the present invention binding peptide domains, in order to maximize binding affinity for the immunogen of the present invention of the resulting product.

In certain other embodiments, the invention contemplates the specific antibodies to the immunogens of the present invention that are multimeric antibody fragments. Useful methodologies are described generally, for example in Hayden et al. 1997, *Curr Opin. Immunol.* 9:201-12; Coloma et al., 1997 *Nat. Biotechnol.* 15:159-63). For example, multimeric antibody fragments may be created by phage techniques to form miniantibodies (U.S. Pat. No. 5,910,573) or diabodies (Holliger et al., 1997, *Cancer Immunol. Immunother.* 45:128-130). Multimeric fragments may be generated that are multimers of Fv region of the immunogen of the present invention, or that are bispecific antibodies comprising the immunogen of the present invention or specific Fv region of the immunogen of the present invention noncovalently associated with a second Fv having a different antigen specificity. See, e.g., Koelemij et al., 1999, *J. Immunother.* 22:514-24. As another example, a multimeric antibody may comprise a bispecific antibody having two single chain antibodies or Fab fragments. According to certain related embodiments, a first Ig fragment may be specific for a first antigenic determinant on an immunogen of the present invention (or variant or fragment thereof), while a second Ig fragment may be specific for a second antigenic determinant of the an immunogen of the present invention. Alternatively, in certain other related embodiments, a first immunoglobulin fragment may be specific for an antigenic determinant of the immunogen of the present invention or variant or fragment thereof, and a second immunoglobulin fragment may be specific for an antigenic determinant on a second, distinct (i.e., non-) molecule. Also contemplated are bispecific antibodies that specifically bind, wherein at least one antigen-binding domain is present as a fusion protein.

The invention also provides an immunoassay for determining the presence or amount of phosphorylated histidine polypeptide in biological samples. The immunoassay of the invention includes a step of contacting the biological sample to be determined with antibodies raised in response to an immunogen of the invention. It is contemplated that any immunoassay for peptides containing at least one phophorylated histidine utilizing haptens, immunogens, and/or antibodies raised against immunogens, are within the scope of the present invention. Examples of immunoassays include radioimmunoassays (RIAs), enzyme immunoassay (EIAs), enzyme-linked-immunosorbent assays (ELISAs) and fluorescent polarization immunoassays (FPIAs), etc. Comprehensive reviews on immunoassay principles, critical components, and assay designs can be readily found in literature. One example is "The Immunoassay Handbook, $3^{rd}$ Edition" by David Wild, Editor (Elservier Science, 2005), another is "Immunoassay," E. P. Diamandis and T. K. Christopoulos, Editors, Academic Press, Inc., 1996.

The immunoassays of the invention may be heterogenous or homogenous. In heterogenous assays, the purpose of the label is simply to establish the location of the molecule to which it is conjugated—i.e., to establish whether the labeled molecule is free in solution or is part of a bound complex. Heterogenous assays generally function by explicitly separating bound antigen-antibody complexes from the remaining free antigen and/or antibody. A method frequently employed consists of attaching an antigen or antibody to a solid surface by covalent bonding, physical absorption or some other means. When antigen-antibody binding occurs, the resulting bound complexes remain attached to the solid surface which is composed of any suitably inert material such as plastic, paper, glass, metal, polymer gel and the like. This allows for separation of free antigen and/or antibody in the surrounding solution by a wash step. A variation of this method consists of using small (typically 0.05 to 20 microns) suspendable particles to provide the solid surface onto which either antibody or antigen is immobilized. Separation is effected by centrifugation of the mixture. Separation is effected by centrifugation of the mixture of sample, reagents and suspendable beads at an appropriate speed, resulting in selective sedimentation of the support particles together with the bound complexes. Alternative solid capture phases, such as magnetic particles, glass beads, plastic tubes, glass wool, latex beads, and the like may also be used.

The capture mechanism may be simply by binding to immobilized secondary antibody or an antigen or to utilize, for example, avidin/streptavidin-biotin type of binding pairs. Natural or manmade binding pairs can be adapted to capture the signals from the rest of the assay mixture.

Signal reporting can be by UV or visible light, fluorescence, luminescence, photon, gold sol, and chemiluminescence, and the like. Furthermore, application of such an antibody include assay variation which utilizes latex beads, liposome, vesicles, and alike to carry signals or signal precursors, and utilize channeling processes, or PCR and alike methods to amplify signals. Furthermore, assay format that are semi-heterogeneous or qusai-heterogeneous (e.g. Roche's Elecsys assay), can also be applied to the assays of the invention.

Use of an enzyme as a label has produced a variety of useful enzyme immunoassays (EIA), the most popular of which is known as ELISA. For a review, see "Enzyme Immunoassay (EIA)/Enzyme-Linked Immunosorbant Assay (ELISA)" by Rudolf M. Lequin, *Clinical Chemistry*, 51: 2415-2418, 2005. In one typical heterogeneous format a competition reaction is employed, in which the ligand of interest, a p-His polypeptide, binds to the specific antibody-enzyme conjugate. After suitable incubation, any remaining free enzyme conjugate is eliminated by washing or other separation methods. A suitable substrate for the enzyme is then brought into contact with the surface containing the bound complexes. The enzyme-substrate pair is chosen to provide a reaction product which yields a readily detectable signal, such as a color change or a fluorescence emission. The use of an enzyme as label services to effectively amplify the contribution of a single labeled bound complex to the measured signal, because many substrate molecules can be converted by a single enzyme molecule.

In another type of assay, an enzyme is covalently coupled to avidin/streptavidin and the resulting enzyme labeled avidin/strepavidin is then mixed or combined with biotin-labeled reagent (i.e., biotin-labeled ligand or biotin-labeled specific binding substance for said ligand) prior to or during utilization of the latter in a specific binding reaction. The basic components in the binding reaction are, in addition to the biotin-labeled reagent, liquid medium or sample (presumed to contain the ligand to be detected) and an insoluble phase containing a specific binding substance for said ligand. The biotin-labeled reagent may be bound to enzyme labeled avidin/streptavidin after it has been mixed or combined with the insoluble phase or, alternatively, the biotin labeled reagent may be pre-combined with enzyme labeled avidin and the resulting conjugate used directly.

Following the specific binding reaction, the enzyme activity of either the insoluble phase or the liquid phase is determined by a suitable detection system; the amount of activity being related to the quantity of ligand in the sample.

For immunoassays with no separation of bound vs. unbound species (homogeneous assays), Enzyme-Mediated Immunoassay (EMIT) exemplifies such an approach. Based on the functional change of an enzyme such as glucose-6-phoshate dehydrogenase, or G6PDH (commonly shown in diminishing activity) of the hapten-enzyme conjugate when bound to the specific antibody, the assay is achieved by contacting sample with an appropriate amounts of antibody and hapten-enzyme conjugate. When there is a large quantity of analyte in the sample, few of the hapten-enzyme conjugates are bound to the antibody (i.e., minimal amount of enzyme activity is attenuated) and the assay mixture exhibits maximal enzyme activity turning over maximal amount of substrate NAD (or NADP) to NADH (or NADPH). By contrast, when there is little analyte present, the majority of the hapten-enzyme conjugates are bound to antibody, and the assay mixture thus reports substantially reduced signal due to diminished enzyme activity.

Thus, the antibodies are selected and characterized for specificity using standard techniques known in the art, such as standard affinity chromatography, dot blot and ELISA assay protocol. The antibody isolated by these techniques recognize the pHis polypeptide but not free histidine or other phosphonoamino acids.

More specifically, the antibodies of the present invention recognize the immunogens of the present invention, such as, for example, polypeptides containing at least the phosphoryltriazolyl alanine moiety thereon. In addition, the antibodies will recognize a phosphorylated histidine, e.g., polypeptides which have at least one phosphorylated histidine thereon, but will not recognize a non-phosphorylated polypeptide or amino acid or a polypeptide in which the phosphorylation is present on amino acids other than histidine and not on any of the histidines present.

In an embodiment, immunogens of various polypeptides are prepared by linking carrier molecules such as KLH through reactive cysteine sulfhydryl group to the polypeptides and then injecting the resulting product into host animals such as rabbits. Then the antibodies are collected and isolated in accordance with techniques known in the art. The sera is screened for antibodies that recognize phosphorylated histidine and polypeptides which have a phosphorylated histidine thereon or compounds of Formula I, such as, phosphoryltriazolyl alanine thereon, but will not recognize a non-phosphorylated polypeptide or amino acid or a polypeptide which is phosphorylated on an amino acid other than histidine and not on histidine.

Another aspect of the present invention is directed to a kit for detecting and determining p-His polypeptides in a sample. The kit includes the polypeptide containing the hapten, or the mixture thereof which may or may not be immobilized and the antibodies of the present invention or a mixture thereof. The kit may optionally include instruction for use of phosphoprotein containing haptens and the antibodies for detecting and or determining the presence of phosphorylated polypeptides comprised of at least one phosphorylated histidine residue.

The preparation of various antibodies by the procedure described opens the door to perform numerous investigations, such as investigation the mechanism of action of the phosphorylation reactions and dephosphorylation reactions. For example, the haptens having SEQ ID. Nos. 1-8, 12, 13, 14 and 21 described hereinbelow when linked to carrier molecules, generate immunogens, and when administered to a host, generates antibodies, which are isolated from the sera thereof. These antibodies are used to study the mechanism of the phosphorylation and dephosphorylation reactions at the molecular level. For example, the H4 p-His antibodies can be used to follow the biochemical enrichment of the histone histidine kinase in nuclear lysates from cultured cells. Extracts derived from regenerating rat liver cells and Walker-256 carcinosarcoma cells, where high histone histidine kinase (HHK) activity has been observed, can be utilized. The nuclei is isolated from cells and the soluble nuclear proteins separated from the chromatin pellet with KCl extraction. The HHK activity in each fraction is evaluated by utilizing the antibodies. Further fractionation is effected using hydroxyapatite chromatography of the solubilized pellet and weak ion exchange chromatography of the soluble nuclear proteins. As the activity is enriched, mass spectroscopy is utilized to identify the proteins in the active fraction. Candidates, in particular those predicted or known to bind ATP, can be generated by recombinant expression in a host animal and assayed for HHK activity in the reconstituted assay with H4.

In another embodiment the present invention is directed to assessing whether a patient has liver cancer or tendency to contract liver cancer. Liver cancer is the third most common cancer in the world. Quite often the diagnosis of liver cancer is too late. As indicated hereinabove, the histone H4 histidine kinase activity is upregulated by 200-fold in human hepatcellular carcinomas compared to normal liver tissue. Thus, there is an abnormal level of phosphorylation of histones if a patient has liver cancer. Since the H4 sequence is highly conserved from yeast to man and is, in fact, invariant around the two histidines at positions 18 and 75, one can utilize the antibodies of the present invention to determine if a patient has liver cancer prior to its manifestation. This is determined by contacting a biological sample such as sera or tissue lysate of a patient suspected of having liver cancer with an antibody of the present invention using any of the immunoassays described hereinabove under conditions sufficient for formation of a complex between the antibody and a phosphopolypeptide in the biological sample in which the histidine is phosphorylated, detecting the presence and determining the concentration of the phospholpolypeptide in the sera and comparing the concentration to normal levels of phosphopolypeptide in the sera, whereupon a significantly enhanced concentration of said complex, e.g., above about 100 times relative to the normal concentration, would indicate that the patient has liver cancer or is at a high risk for liver cancer and treatment can be started early.

The following non-limiting examples further illustrate the present invention.

General Methods

Unless otherwise specified, all reactions were carried out in an oven-dried (>110° C.) round-bottom flask equipped with a Teflon™ coated magnetic stir bar and a rubber septum under a positive pressure of argon. Sensitive solvents and reagents were transferred by syringe or stainless steel cannula. Reactions were run at room temperature (20-25° C.) unless otherwise noted. Unless otherwise specified, reaction temperatures refer to the external temperatures of the bath in which the reaction vessel was partially immersed. The term "0° C." refers to an ice-water bath and the term "-78° C." refers to a dry ice-isopropanol bath.

The terms "removal of the solvent in vacuo" and "concentration" refer to evaporation of solvent using a Büchi rotary evaporator equipped with a vacuum pump. Residual solvents were removed from nonvolatile samples using a vacuum line held at 0.1-1.0 mmHg.

Materials

*E. coil* BL21(DE3) and pLysS cells were purchased from Novagen (Madison, Wis.). Criterion 15% and 4-20% Tris HCl, and Criterion 5% TBE gels were purchased from BioRad (Hercules, Calif.). Amino acid derivatives, MBHA resin, and coupling reagents were purchased from Nova biochem (San Diego, Calif.). Primer synthesis and DNA sequencing were performed by Integrated DNA Technologies and Genewiz, respectively. All other chemical reagents were purchased from Sigma-Aldrich (Milwaukee, Wis.) or Fisher Scientific (Pittsburgh, Pa.).

Unless otherwise noted, all commercial reagents, solvents, and solutions were used without further purification. Dichloromethane ($CH_2Cl_2$) and Tetrahydrofuran (THF) were passed through an alumina drying-column (Sols-tek Inc.). Deuterated chloroform was passed through a pad of basic alumina and stored over anhydrous potassium carbonate.

Chromatography

Analytical thin-layer chromatography (TLC) was performed by using glass or aluminum-backed silica plates coated with a 0.25 mm thickness of silica gel 60 $F_{254}$ (Merck), visualized with an ultraviolet light, followed by exposure to p-anisaldehyde solution, potassium permanganate solution, p-bromocresol green, or ceric ammonium molybdate solution followed by heating.

The term "flash column chromatography" refers to column chromatography using Merck silica gel 60 (230-400 mesh) as described by Still et al. *J. Org. Chem.* 1978, 43, 2923-2221. The eluent composition is indicated following the description of purification (percentage of the more polar solvent in the less polar solvent).

Analytical and semi-preparative scale reverse-phase HPLC (RP-HPLC) were performed on a Hewlett-Packard 1100 series instrument using Vydac C18 columns (4×150 mm; 10×250 mm) at 1 and 4 mL/min, respectively. Unless otherwise noted, all analytical gradients were 0-73% B over 30 min (A: 0.1% trifluoroacetic acid (TFA) in water; B: 90% acetonitrile, 0.1% TFA in water). Preparative and process scale RP-HPLC were performed on a Waters DeltaPrep 4000 system connected to a Waters 486 tunable detector using Vydac C18 columns (22×250 mm; 50×250 mm) at 15 and 30 mL/min, respectively.

Size-exclusion chromatography was performed on an AKTA FPLC system from GE Healthcare equipped with a P-920 pump and a UPC-900 monitor.

Physical and Spectroscopic Data

Optical rotations were measured on a JASCO P-2000 digital polarimeter using solutions in indicated solvents. All values are reported in the following format: $[\alpha]_D$(temperature of measurement)=specific rotation (concentration of the solution reported in units of 10 mg sample per 1 mL solvent, solvent used).

Proton, carbon, and phosphorus NMR spectra were measured on either a Bruker Avance DPX-400 ($^1H$ at 400 MHz, $^{13}C$ at 100 MHz) magnetic resonance spectrometer or a Bruker Avance DMX-600 ($^1H$ at 600 MHz). $^1H$ chemical shifts are reported in parts per million (ppm) using residual $CHCl_3$ (d 7.26) as the internal standard, coupling constants (J) are reported in Hertz (Hz). Proton ($^1H$) NMR information is tabulated in the following format: multiplicity, number of protons, coupling constant, and structural assignments. Multiplicities are reported as follows: s=singlet, brs=broad singlet, d=doublet, t=triplet, q=quartet, sept=septet, dd=doublet of doublets, td=triplet of doublets, ddd=doublet of doublet of doublets, dddd=doublet of doublet of doublet of doublets, m=multiplet. Proton decoupled $^{13}C$ NMR spectra are reported in ppm (δ) relative to residual $CHCl_3$ (δ 77.0) unless noted otherwise.

Example 1

Boc-Azidoalanine (8)

This compound was prepared via the root of Chamberlin, as described in Aggen, J. B.; Humphrey, J. M.; Guass, C. M.; Huang, H. B.; Nairn, A. C.; Chamberlin, A. R., *Bioorg. Med. Chem.* 1999, 7, 543-564, the contents of which are incorporated by reference.

Example 2

Diethyl Ethynylphosphonate (9)

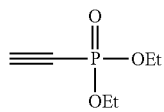

This known compound was synthesized according to the procedure of Acheson et al. in *J. Chem. Reso*; (Miniprint), 1986, 3001-3019 with some modifications. In a 100-mL round bottom flask equipped with a magnetic stir bar, trimethylsilylacetylene (2.9 mL, 21 mmol) was dissolved in dry THF (40 mL) at room temperature under argon atmosphere. The mixture was cooled to −78° C. and n-butyl-lithium (14 mL of 1.6M in hexane, 22 mmol) was added dropwise over 3 min. In a separate round-bottom flask, diethyl chlorophosphate (10 mL) was dissolved in dry THF (10 mL) and was added to the solution of lithium trimethylsilylacetylide dropwise over 25 min via a cannula. The mixture was stirred at −78° C. for 1 h until trimethylsilylacetylene was consumed, as observed by TLC. Two new spots appeared on TLC($R_f$=0.8 and 0.6 eluted with ethyl acetate, visualized with $KMnO_4$ stain). The reaction mixture was warmed up to room temperature and saturated aqueous $Na_2CO_3$ (100 mL) was added. The mixture was extracted with ethyl acetate (3×50 mL) and concentrated under reduced pressure to give dark brown syrup. This crude material was dissolved in methanol (20 mL) and $Na_2CO_3$ (500 mg) was added. Aqueous 1 N NaOH was then added dropwise until the pH the solution was 10 (by a pH paper). Within 30 min, the two spots on TLC converged into the lower $R_f$ spot ($R_f$=0.6, eluted with ethyl acetate, visualized with $KMnO_4$ stain). The reaction mixture was diluted with water and extracted with ethyl acetate (3×30 mL) The combined aqueous phases were dried over $MgSO_4$ (s), filtered, and concentrated in vacuo. The crude product (pale yellow syrup) was purified by silica gel flash chromatography (30% ethyl acetate in hexane) to give 1.45 g of colorless syrup (yield=45%). The analytical data are identical with those reported by Acheson et al.

Example 3

(S)-2-(tert-butoxycarbonylamino)-3-(4-(diethoxy-phosphoryl)-1H-1,2,3-triazol-1-yl)propanoic acid (10)

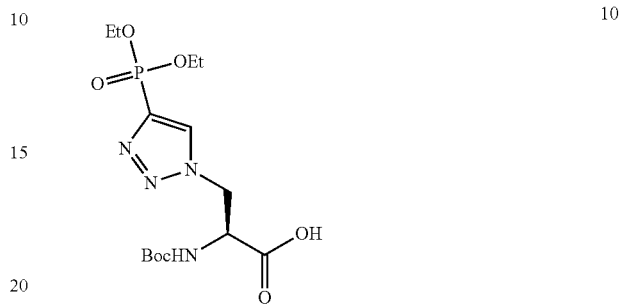

In a round bottom flask equipped with a magnetic stir bar, Boc-azidoalanine 8 (490 mg, 2.13 mmol, prepared via the route of Chamberlin as described in *Biorg Med. Chem.* 1999, 7, 543-564 and diethyl ethynylphosphonate 9 (414 mg, 2.5 mmol) were dissolved in DMF (10 mL) at room temperature. Under argon atmosphere, diisopropylethylamine (750 µL, 4.3 mmol) and CuI (81 mg, 0.43 mmol) were added respectively, and the mixture was stirred at room temperature for 4 h until TLC indicated the consumption of Boc-azidoalanine ($R_f$=0.45, eluted with $CHCl_3$:MeOH:AcOH=90:8:2). The reaction mixture was diluted with 20 mL of ethyl acetate and extracted with 3×20 mL water. The aqueous phase was pH ~8. Combined aqueous phases were acidified with 2N HCl until pH=3, and were extracted with ethyl acetate (5×20 mL) The combined organic phases were washed with brine (2×10 mL), dried over $MgSO_4$ (s), filtered, and concentrated in vacuo. The crude yellow syrup was purified by process RP-HPLC (10-40% solution B over 1 h, 30 mL/min) Some mixed fractions were combined, lyophilized and re-purified by process C18 RP-HPLC (20-55% solution B over 1 h, 30 mL/min) Lyophilization of combined fractions containing the product afforded 775 mg of colorless syrup (72% yield).

$R_f$=0.10 (eluted with $CHCl_3$:MeOH:AcOH=90:8:2, a yellow spot visualized with p-bromocresol green stain)

$^{31}P$ NMR ($CDCl_3$): 8.13 ppm.

$^1H$ NMR (400 MHz, $CDCl_3$): 9.62 (brs, 1H, acid), 8.28 (s, 1H, triazole), 5.55 (s, 1H, NH), 4.97 (brs, 2H, β-$CH_2$), 4.76 (brs, 1H, α-CH), 4.10-4.27 (m, 4H, $OCH_2CH_3$), 1.43 (s, 9H, t-butyl), 1.33 (t, J=7.2 Hz, 6H, $OCH_2CH_3$).

$^{13}C$ NMR (100 NMR, $CDCl_3$): 170.64, 155.79, 136.62 (d, $J_{C-P}$=241 Hz), 132.97 (d, $J_{C-P}$=34 Hz), 81.20, 64.27 (t, $J_{C-P}$=6.3 Hz), 54.02, 51.57, 28.64, 16.50 (d, $J_{C-P}$=6.4 Hz) ppm.

FT-IR (on NaCl plate): 3130, 2981, 2105, 1714, 1507, 1368, 1240, 1205, 1163, 1023, 979, 754 $cm^{-1}$.

$[α]_D$ (at 294K)=+60° (c=1.0 in $CHCl_3$).

HRMS=393.1534 (calculated for $[M+H^+]^+$, $C_{14}H_{26}N_4O_7P$), 393.1530 (observed). HPLC retention time=16.5 min (C18 analytical column, 0-73% solution B over 30 min, 1 mL/min).

Example 4

Boc-Azidoalanine Benzyl Ester (11)

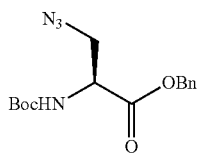

Boc-azidoalanine 8 (520 mg, 2.26 mmol) was dissolved in dry acetonitrile (8 mL) in glass vial equipped with a magnetic stir bar and capped with a septum. Benzyl bromide (325 μL, 2.71 mmol) and diisopropylethylamine (440 μL, 2.49 mmol) were subsequently added via syringe. The solution was stirred for 18 h at room temperature until TLC indicated the consumption of the starting material. The reaction mixture was concentrated in vacuo and the crude product was loaded onto a silica gel column. The column was eluted first with 10% ethyl acetate/hexane to wash off the residual benzyl bromide and then with 20% ethyl acetate/hexane to elute the product (452 mg, 63% yield).

$^1$H NMR (400 MHz in CDCl$_3$): 7.27-7.42 (m, 5H, aromatic), 5.40 (brs, 1H, NH), 5.23 (t, 2H, J=12.8 Hz, benzylic), 4.52 (brs, 1H, α-CH), 3.75 (d, 2H, J=2.3 Hz, β-CH$_2$), 1.46 (s, 9H, t-butyl) ppm.

$^{13}$C NMR (100 MHz in CDCl$_3$): 170.09, 155.47, 135.30, 129.10, 129.06, 128.79, 80.91, 68.19, 54.07, 53.09, 28.67 ppm.

FT-IR (film on NaCl): 3433, 3367, 2980, 2017, 1745, 1714, 1499, 1368, 1348, 1160, 1047 cm$^{-1}$.

$[α]_D$ (at 294K)=+8.0° (c=1.0 in CHCl$_3$).

ESI-MS: 343.1 (calculated for [M+Na]$^+$C$_{15}$H$_{20}$NaN$_4$O$_4$), 343.3 (observed).

Example 5

(S)-2-(tert-butoxycarbonylamino)-3-(5-(diethoxyphosphoryl)-1H-1,2,3-triazol-1-yl)propanoic acid (12)

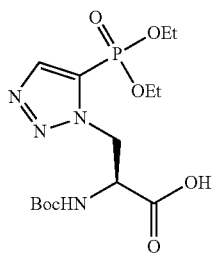

Boc-azidoalanine benzyl ester 11 (360 mg, 1.13 mmol) and diethyl ethynylphosphonate 9 (370 mg, 2.26 mmol) were dissolved in dry toluene (4 mL) in a round bottom flask and degassed by free-pump-thaw (3 cycles). In a separate round bottom flask equipped with a magnetic stir bar, Cp*Ru(COD)Cl wherein COD is η$^4$-cyclooctadiene (65 mg, 0.15 mmol) and Cp* is η$^5$-C$_5$Me$_5$ was dissolved in degassed toluene (3 mL) under argon atmosphere. To this, the solution of the azide and alkyne was added dropwise via a cannula over 1 min. The resultant solution was stirred at room temperature under argon for 1.5 h while being monitored by TLC. The reaction mixture was directly loaded to a pad of silica gel (10 cm×3 cm diameter, packed with 10% ethyl acetate/hexane) and eluted with 60% ethyl acetate/hexane to remove the ruthenium catalyst. The cycloaddition product was not further purified but used directly in the subsequent deprotection step because the product and the unreacted alkyne have very similar mobility on silica gel (R$_f$=0.3, 50% ethyl acetate/hexane, a brown spot stained with p-anisaldehyde).

The crude product was concentrated in vacuo and was re-dissolved in ethyl acetate (10 mL) in a round bottom flask equipped with a magnetic stir bar. To this crude product mixture, Pd on carbon (45 mg, 10% w/w) was added and the suspension was vigorously stirred at room temperature for 4 h under an H$_2$ atmosphere maintained by a balloon. The reaction mixture was directly loaded onto a pad of silica gel and was eluted first with ethyl acetate to remove nonpolar byproducts and then with a mixture of CHCl$_3$:MeOH:AcOH (89:10:1 by volume) to elute the crude product. The crude product was concentrated in vacuo and purified by process RP-HPLC (Vydac C18 columns, 50×250 mm) in a gradient of 15-60% solvent B over 60 min at 30 mL/min. Lyophilization of the pooled product fractions afforded 277 mg of colorless syrup (68% yield over two steps).

$^{31}$P NMR (125 MHz, CDCl$_3$): 4.58 ppm $^1$H NMR (600 MHz, CDCl$_3$): 10.11 (brs, 1H, acid), 8.01 (s, 1H, triazole), 5.96 (brs, 1H, NH), 5.09 (dd, 1H, J=4.8 Hz, 11.6 Hz, α-CH), 4.93 (d, 2H, J=6.1 Hz, β-CH$_2$), 4.22-4.30 (m, 4H, OCH$_2$CH$_3$), 1.41 (t, 6H, J=4.3 Hz), 1.39 (s, 9H, t-butyl) ppm.

$^{13}$C NMR (100 MHz, CDCl$_3$): 171.46, 155.88, 140.67 (d, J$_{C-P}$=33 Hz), 127.22 (d, J$_{C-P}$=222 Hz), 80.85, 64.63, 53.82, 51.57, 28.63, 16.55 (t, J=7.2 Hz).

FT-IR (film on NaCl): 3310, 2982, 1716, 1505, 1445, 1394, 1368, 1251, 1165, 1018, 983 cm$^{-1}$.

$[α]_D$ (at 294K)=+1.8° (c=1.0 in CHCl$_3$).

LRMS (ESI): m/z=415.2 (M+Na$^+$), 393.0 (M+H$^+$), 358.8 (M-tButyl+Na$^+$), 336.8 (M-tButyl+H$^+$), 315.2 (M-Boc+Na$^+$), 293.0 (M-Boc+H$^+$).

HRMS=393.1534 (calculated for [M+H$^+$]$^+$, C$_{14}$H$_{26}$N$_4$O$_7$P), 393.1530 (observed).

HPLC retention time=17.1 min (C18 analytical column, 0-73% solution B over 30 min, 1 mL/min).

Example 6

Thermal Cycloaddition Between 8 and 9

In a dried glass vial equipped with a magnetic stir bar, Boc-azidoalanine 8 (27 mg, 0.12 mmol) and diethyl ethynylphosphonate 9 (21 mg, 0.13 mmol) were dissolved in DMF (0.5 mL) The atmosphere was flushed with argon, and the vial was sealed and heated to 90° C. for 15 h until TLC indicated the total consumption of Boc-azidoalanine. The reaction mixture was concentrated in vacuo, and the crude product mixture was analyzed by $^1$H NMR, which is provided in FIG. 1. The integration of peaks showed that it contains a ~4:1 mixture of 10 and 12.

Example 7

Peptide Synthesis

Peptide-amides were manually synthesized on MBHA resin (0.1 mmol scale) following the in situ neutralization/HBTU activation protocol as described in Schnolzer, M.; Int. J. Pept. Protein Res. 1992, 40, 180-193. The α-thioester peptide was synthesized (0.1 mmol scale) using 3-mercaptopropionamide linker as in accordance with the procedure described by Camarero, J. A. et al.; In Current Protocols in Protein Science John E. Coligan, J. E.; Dunn, B. M.; Speicher, D. W.; Wingfield, P. T., Eds.; John Wiley and Sons: New York, 2001; Unit 18.4. The scheme is provided hereinbelow.

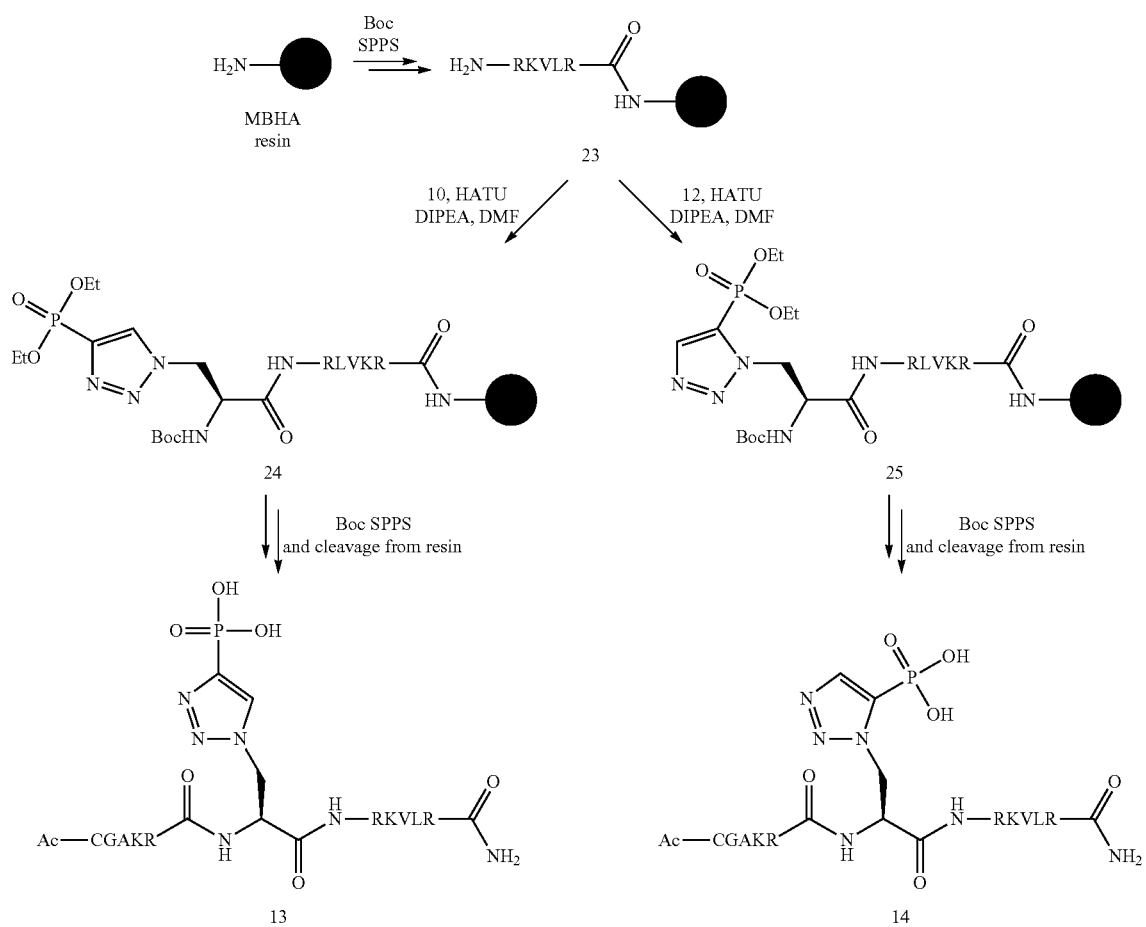

In the scheme above, 23 is identified as SEQ ID #9, 24 as SEQUENCE ID #10 and 25 as SEQUENCE ID #11.

For the coupling of the compounds of Formula I, 2 equivalents of the compound of Formula I and 1.9 equivalents of HATU (2-(7-Aza-1H-benzotriazole-1-yl)-1,1,3,3-tetramethyluronium hexafluorophosphate) were used in place of HBTU. The assembled peptide was cleaved from the resin using anhydrous HF with 4% (v/v) p-cresol at 0° C. for 1 h. The crude peptide was treated with Tris(2-carboxyethyl)phosphine hydrochloride (TCEP•HCl) to reduce the disulfide and then purified by preparative or process RP-HPLC.

Peptide 13 (SEQUENCE ID #12)

Isolated yield 28% (based on initial resin loading)

EST-MS: 1445.6 (calculated); 1446.0 (observed))

HPLC retention/time: 13.7 min (C18 Vydac column, 5-25% solution B over 30 min, 1 ml/min)

Peptide 14 (SEQUENCE ID #13)

Using the procedure as above, the following peptides were prepared

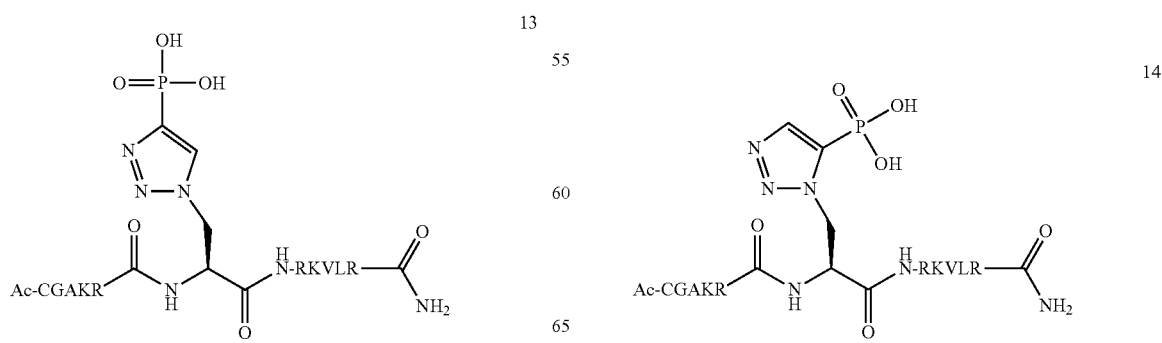

Isolated yield: 22% (based on initial resin loading)

ESI-MS: 1445.6 (calculated); 1445.7±0.5 (observed).

HPLC retention time: 9.40 min (C18 Vydac column, 0-73% solution B over 30 min, 1 mL/min)

Peptides 15-18 were synthesized on a Rink-amide resin by an automated peptide synthesizer (CEM Liberty) via Fmoc chemistry. For the phosphoamino acid residues, monobenzyl-protected phosphoamino acids were used. The peptide was cleaved from the resin with a mixture of trifluoroacetic acid, triisopropylsilane, water (95:2.5:2.5). The crude peptide was treated with Tris(2-carboxyethyl)phosphine hydrochloride (TCEP•HCl) to reduce the disulfide and then purified by preparative or process RP-HPLC.

Peptide 15 (SEQUENCE ID #14)

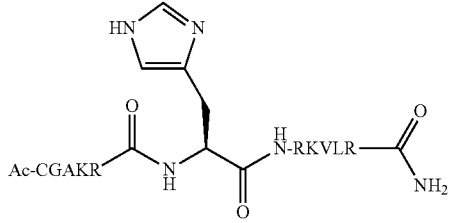

15

ESI-MS: 1363.80 (calculated); 1364.34±0.15 (observed).

HPLC retention time: 9.61 min (C18 Vydac column, 0-73% solution B over 30 min, 1 mL/min)

Peptide 16 SEQUENCE ID #15

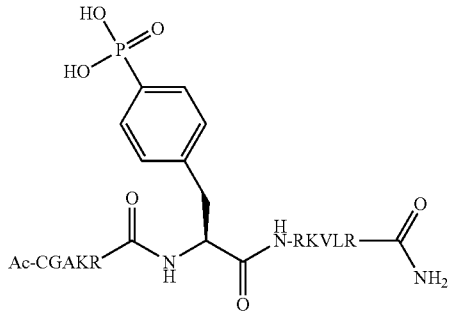

16

ESI-MS: 1470.68 (calculated); 1471.02±1.01 (observed).

HPLC retention time: 9.84 min (C18 Vydac column, 0-73% solution B over 30 min, 1 mL/min)

Peptide 17 SEQUENCE ID #16

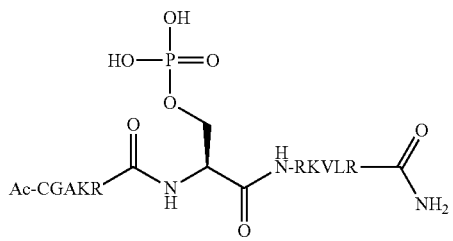

17

ESI-MS: 1394.58 (calculated); 1394.35±0.65 (observed).

HPLC retention time: 9.33 min (C18 Vydac column, 0-73% solution B over 30 min, 1 mL/min)

Peptide 18 SEQUENCE ID #17

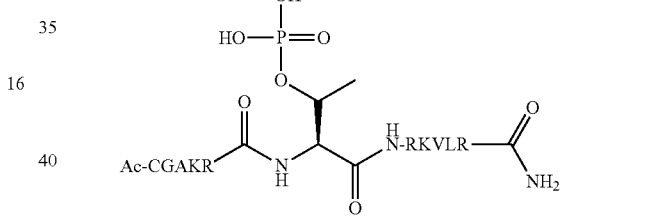

18

ESI-MS: 1408.61 (calculated); 1408.01±0.01 (observed).

HPLC retention time: 9.25 min (C18 Vydac column, 0-73% solution B over 30 min, 1 mL/min)

Peptide 19 (SEQUENCE ID #18)

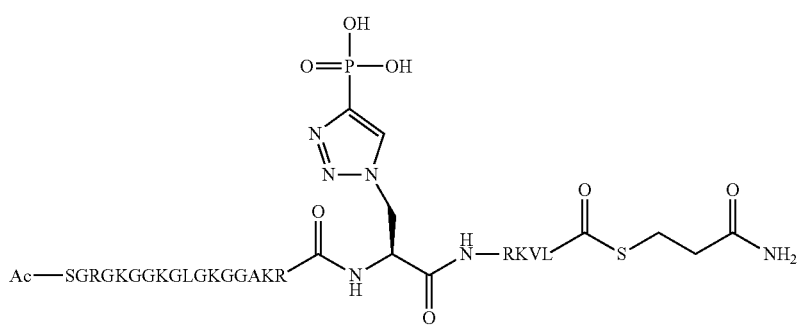

19

Peptide 19 was prepared utilizing the procedure described hereinabove for peptides 13 and 14.

Isolated yield: 15% (based on initial resin loading)

ESI-MS: 2414.7 (calculated); 2416.5±1.2 (observed).

HPLC retention time: 13.09 min (C18 Vydac column, 0-73% solution B over 30 min, 1 mL/min)

Example 8

Preparation of Recombinant Histones

Recombinantly expressed *Xenopus laevis* histone H4 was prepared according to the procedure of McCinty et al. in Nature 2008, 453, 812, the contents of which are incorporated by reference. H4 mutants were generated with a QuikChange II XL kit (Stratagene) according to the manufacturer's instructions, using the following primers and *Xenopus* H4 expression plasmid:

```
H4H18A-Forward
                              Sequence ID #24
(5'-GTAAAGGTGGTGCTAAACGTGCGCGTAAAGTTCTGCGTGAC-3')

H4H18A-Reverse
                              SEQUENCE ID #19
(5'-GTCACGCAGAACTTTACGCGCACGTTTAGCACCACCTTTAC-3')

H4H75A-Forward
                              SEQUENCE ID #20
(5'-TGACGCTGTTACCTACACCGAAGCCGCTAAACGTAAAACC-3')

H4H75A-Reverse
                              SEQUENCE ID #21
(5'-GGTTTTACGTTTAGCGGCTTCGGTGTAGGTAACAGCGTCA-3')
```

H4 (Δ1-22) R23C and H4R23C mutants were prepared as reported in Shogren-Knaak, M. et al; *Science* 2006, 311, 844. The resulting histone expression plasmids were verified by DNA sequencing.

For protein expression, *E. coli* BL21(DE3)pLysS cells, transformed with the appropriate histone expression plasmid, were grown in Luria-Bertani (LB) media at 37° C. until $OD_{600}$=0.6, and protein expression was induced by the addition of 0.2 mM IPTG (1 mM IPTG for H4 Δ1-22 R23C) at 37° C. for 2-3 h. Cells were harvested and recombinant histone was purified as described in McGinty et al. For the H4 (Δ1-22) R23C mutant, an additional step was taken (incubation of the crude histone in 200 mM methoxylamine, pH 5, room temperature, 12 h) before the final HPLC purification to ensure the N-terminal Cys residue is unmasked.

The purity and identity of the recombinant proteins was established by SDS-PAGE, analytical HPLC and ESI-MS. The actual analytical data are given below and in FIGS. 6-9.

H4H18A: HPLC retention time: 15.7 min (30-80% B over 30 min, 1 mL/min) ESI MS: 11171.4±3.6 (expected 11170.0)

H4H75A: HPLC retention time: 16.5 min (30-80% B over 30 min, 1 mL/min) ESI MS: 11172.1±3.7 (expected 11170.0)

H4(Δ1-22) R23C: HPLC retention time: 155 min (30-80% B over 30 min, 1 mL/min) ESI MS: 8999.3±1.0 (expected 8996.5)

HHR23C: HPLC retention time 123.9 min (0-73% B over 30 min, 1 mL min ESI MS: 11183.6±2.4 (expected 11183.1)

Example 9

Generation of Polyclonal Antibody Ab-3pHis

The antisera generation and affinity purification was performed at Active Motif, Inc. (Lake Placid, N.Y.). The rabbit polyclonal antisera were raised against the N-terminal tail fragment of histone H4 (peptide 13) containing an N-term Cys residue. Peptide 13 was conjugated to KLH carrier protein via maleimide chemistry using Sulfo-SMCC (Pierce). Four rabbits were injected with the peptide/KLH conjugate using a standard immunization protocol and individual bleeds were screened for detection of the phosphohistidine modification by dot blots using the unmodified peptide as a control.

Affinity beads were prepared by immobilizing 2 mg of the non-modified H4 peptide 15 (Ac-CGAKRHKVLR-NH$_2$, SEQUENCE ID #14) to agarose beads using Pierce Sulfo-Link Immobilization Kit® as per the manufacturer's instructions. Rabbit sera was depleted of reactivity to the unmodified peptide by incubating 10 mL of the sera with the peptide beads and then recovering the unbound as purified antibody Ab-3pHis.

Figure 2:
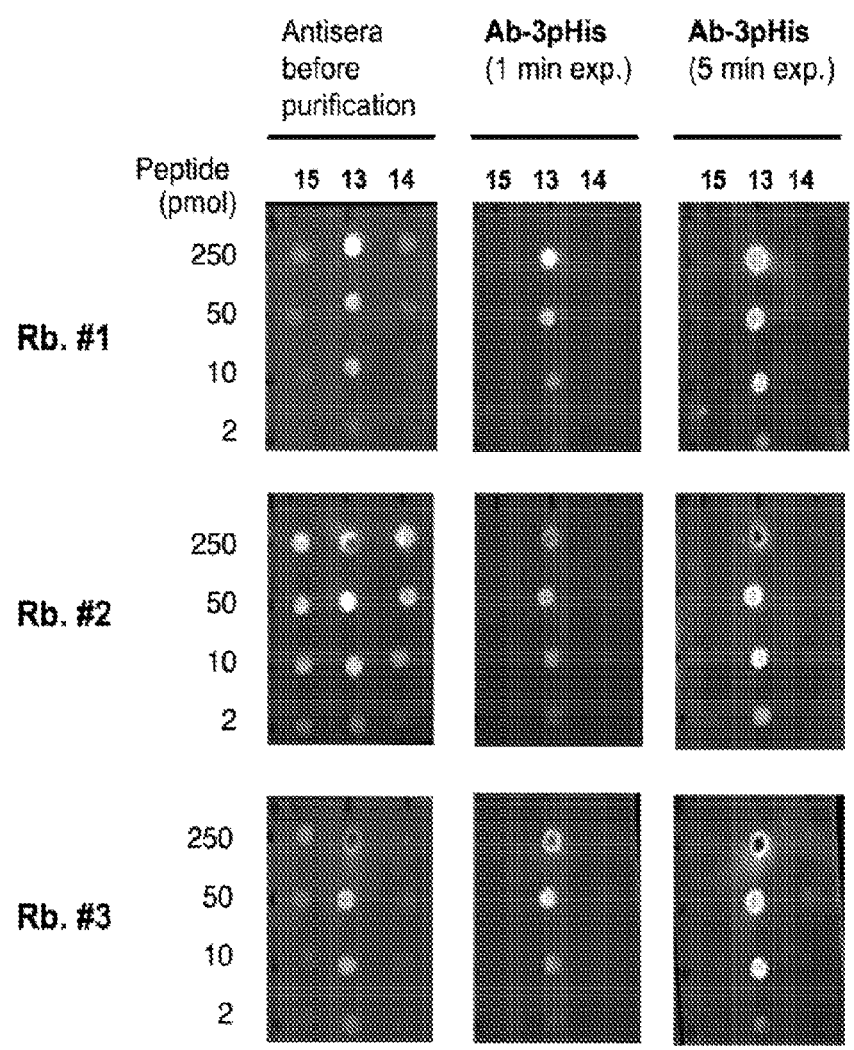
FIG. 2 is a peptide dot blot using peptides 13, 14 and non-modified H4 peptide 15. Different batches of antisera raised against peptide 13 in three rabbits, rabbit #1, rabbit #2 and rabbit #3, were tested. They show the images of antisera before purification, 1 minute after exposure and 5 minutes after exposure.
Figure 3:
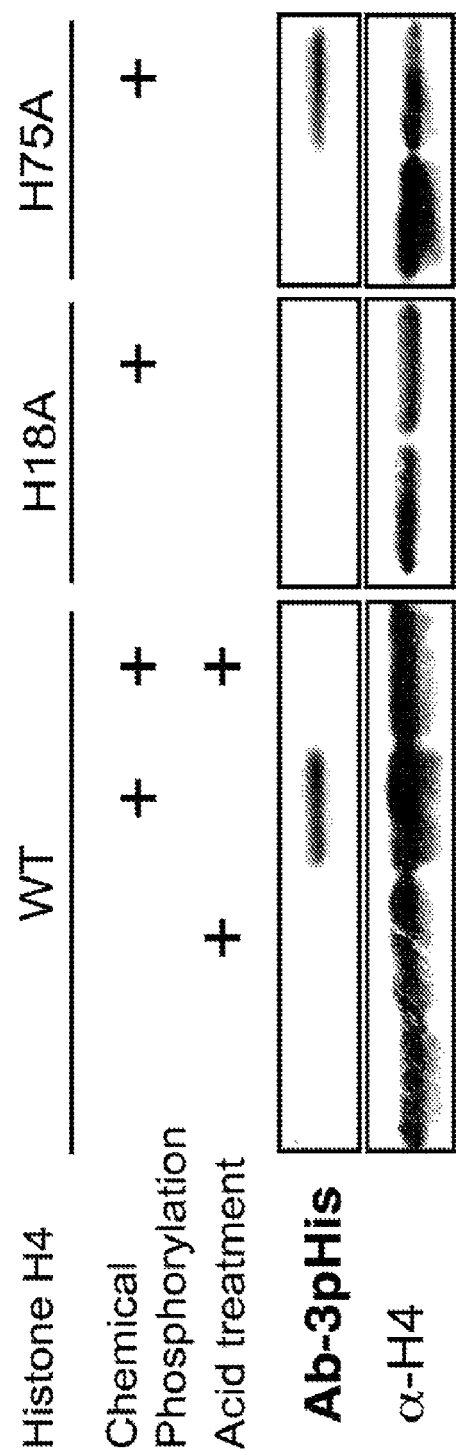
FIG. 3 is a western blot of recombinant histone H4 and mutant using Ab-3pHis and as a loading control, anti-H4 antibody. The initial anti-pHis blot with Ab-3-pHis was stripped and re-probed with an alpha H4 antibody.

The dot blots are depicted in FIG. 2. 2 μL of a 5-fold serial dilution of the peptide (15, 13, and 14) starting at 125 μM were spotted onto PVDF membranes. Membranes were first blocked in 5% non-fat dry milk in TBS-Tween (0.05%) (5% NFDM/TBST) and then incubated with rabbit sera at 1/1000 dilution in 5% NFDM/TBST overnight at 4° C. Membranes were washed and incubated with goat anti-rabbit IgG-HRP conjugate in 5% NFDM/TBST for 45 min at room temperature. Membranes were then washed and incubated with SuperSignal West Dura ECL substrate (Pierce). Images were captured on a CCD camera system (Syngene).

The results are depicted in FIG. 2, which depict peptide dot blots using 13, 14 and non-modified H4 peptide H15. Different batches of antisera raised against 13 in three rabbits were tested. Before the affinity depletion, background signals from the unmodified peptide are noticeable. Batches of Ab-3pHis obtained after the affinity depletion using 15 show the background signals in a negligible level even in overexposed (5 min) images.

Figure 10:
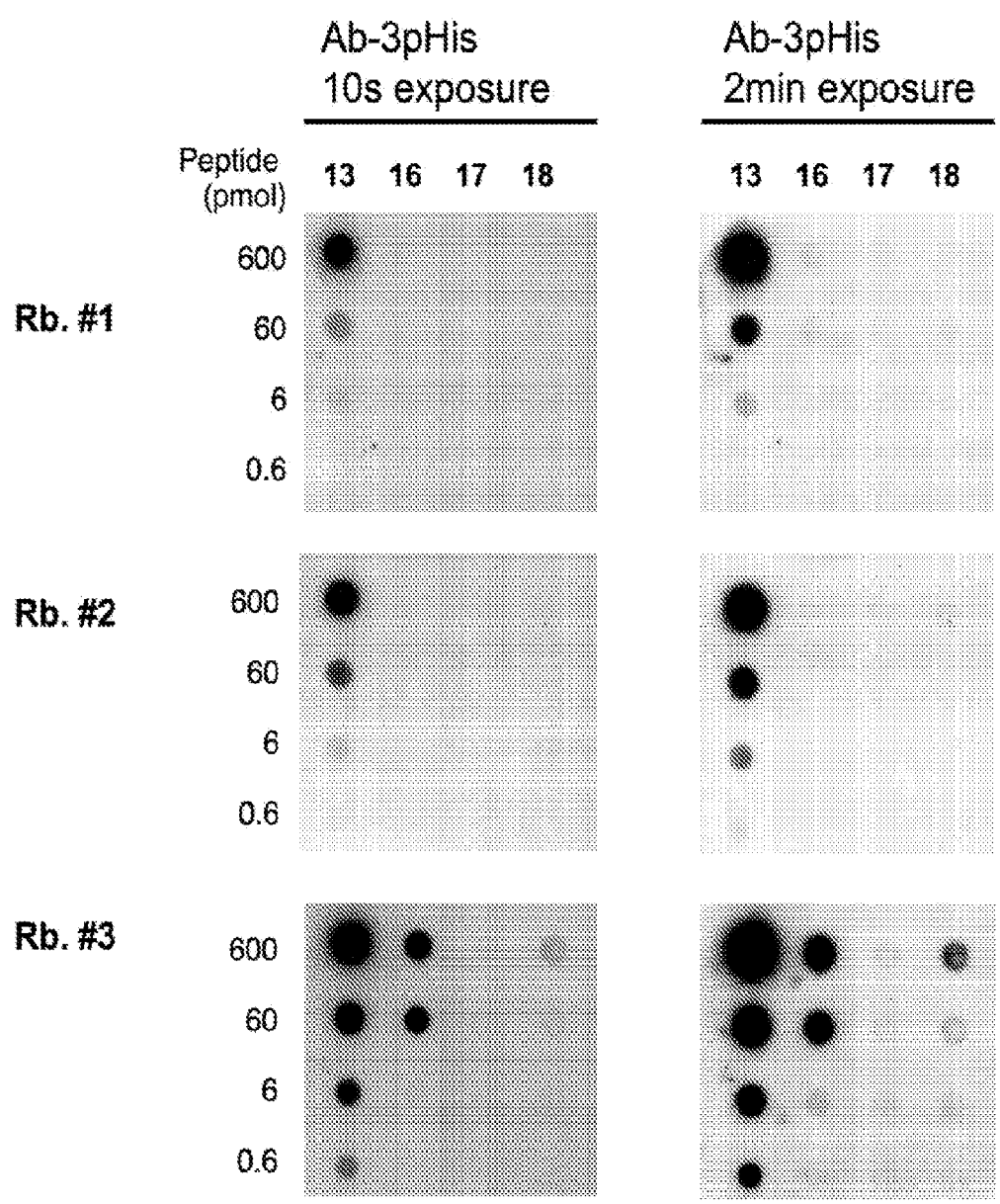
FIG. 10 is the peptide dot plot using peptides 13, 16, 17 and 18.

For fluorescein labeling of the peptides, peptides 13-18 were dissolved in PBS (final concentration 1 mM) and 5-iodoacetamidofluorescein (5-IAF) (2-5 equivalents as a solution in DMF) was added. The pH was adjusted to 7 using 0.01N NaOH solution and the mixture was incubated overnight at room temperature in the dark. Unreacted 5-IAF was purified away by reverse-phase HPLC. The fluorescein-labeled peptides were lyophilized, re-dissolved in PBS, and quantified with using the molar extinction coefficient of fluorescein (65000 M$^{-1}$ cm$^{-1}$ at 490 nm). The peptides were used for the dot blot assays described above. The dot blots are depicted in FIG. 10 using peptides 13, 16, 17, and 18. The antibody Ab-3pHis from rabbit #3 shows some degree of cross-reactivity (<10%) to the pTyr peptide (16) and pSer

(18) peptide. For other batches of Ab-3pHis, the cross-reactivity to other phosphoamino acids is negligible.

To determine the cross-reactivity of Ab-3pHis towards the phosphorylated histene H4, recombinant H4 protein was chemically phosphorylated on histidines in 3-pHis form.

Example 10

Chemical Phosphorylation of Histone H4

Chemical phosphorylation of purified recombinant histone H4 was performed following the procedure of Zu et al. *Amino Acids* 2007, 32, 347-357. For acid-treated samples, the phosphorylated histone solution (1 mg/mL, 10 µL) was acidified with 1 N HCl (5 µL), incubated at 37° C. for 15 min, and neutralized with 1 N NaOH (5 µL).

Example 11

SDS-PAGE and Western Blot Analysis

Figure 5:
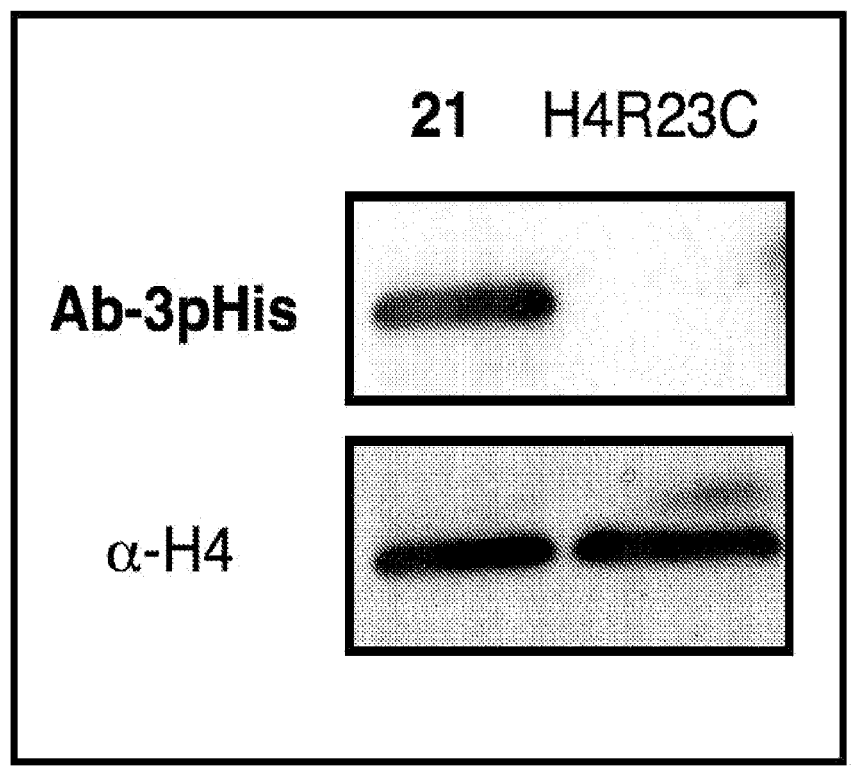
FIG. 5 is the western blot analysis of recombinant H4 and H4R23C mutant using Ab3-pHis and full length histone H4.
Figure 6:
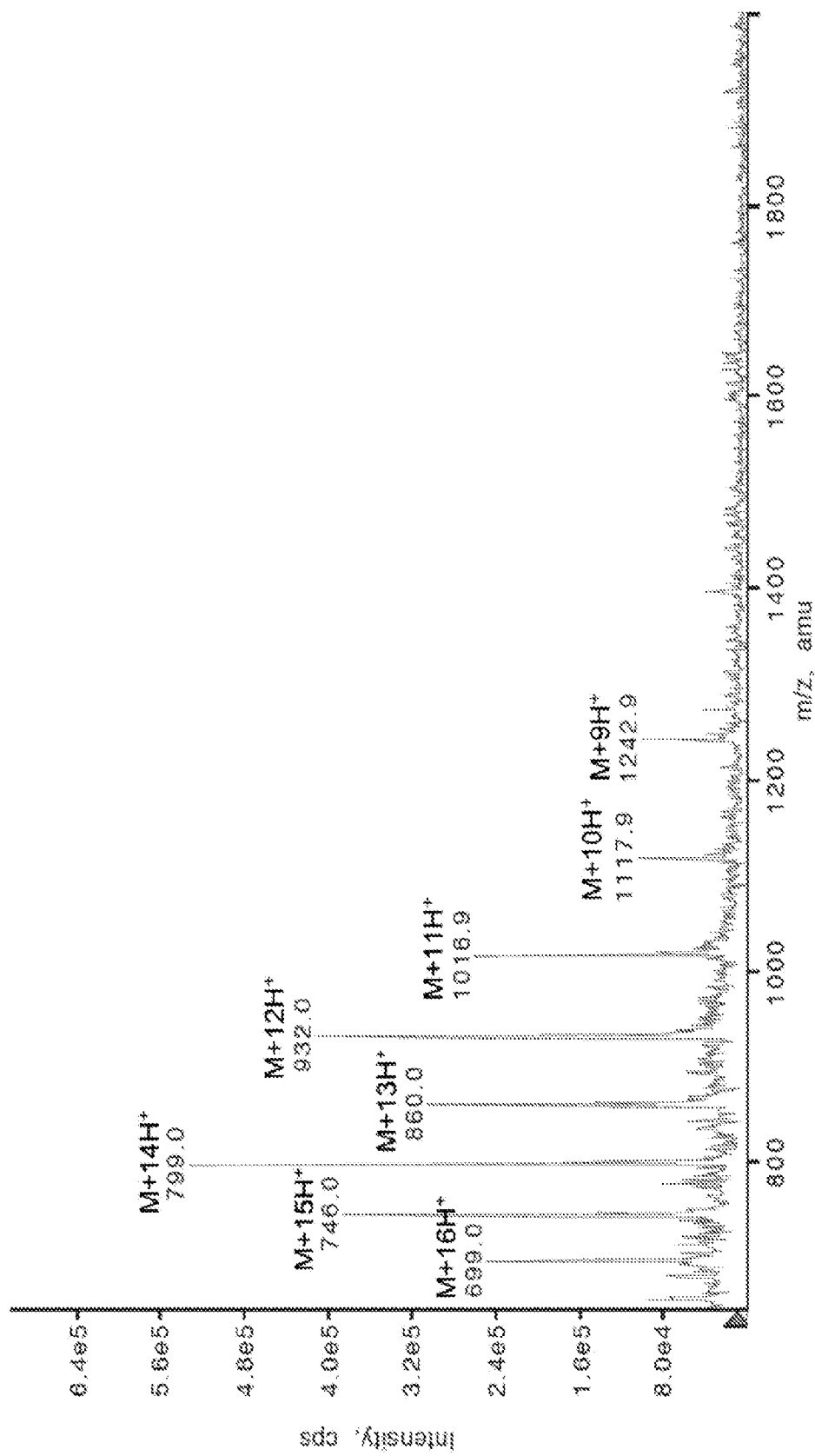
FIG. 6 is the ESI MS of 44H18A, as defined herein.
Figure 7:
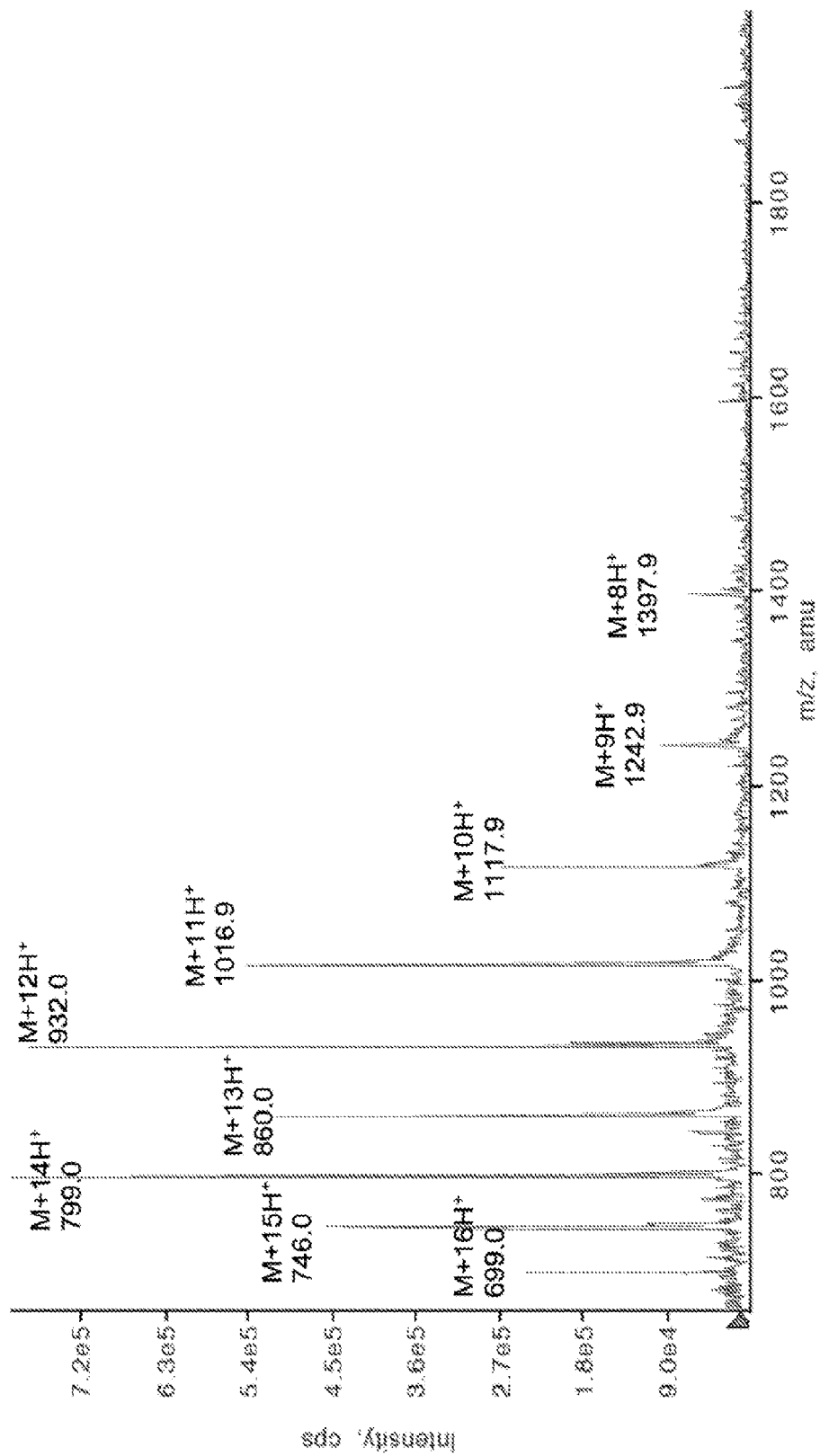
FIG. 7 is the ESI MS of H4H75A, as defined herein.
Figure 8:
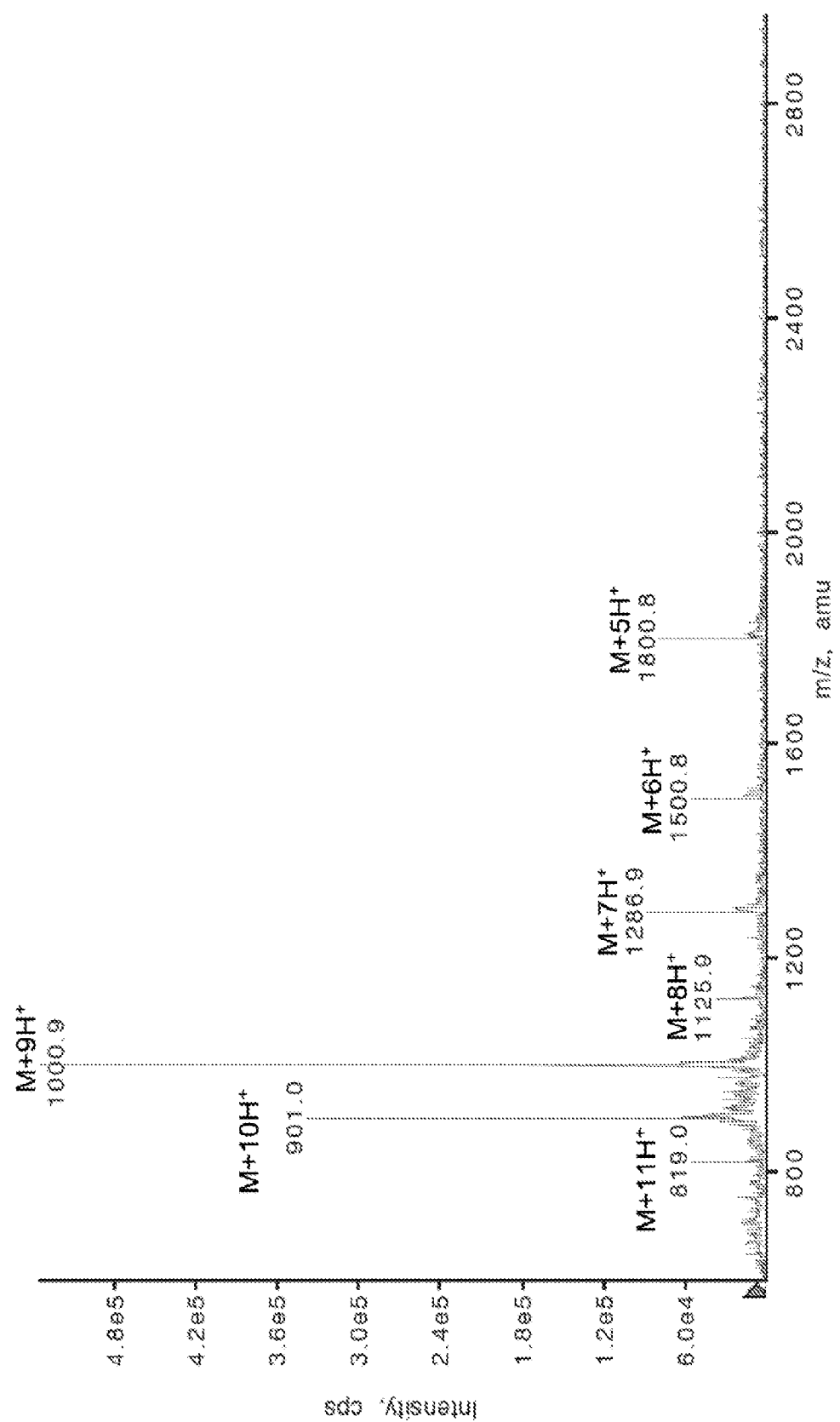
FIG. 8 is the ESI MS of H4(Δ1-22) R23C.
Figure 9:
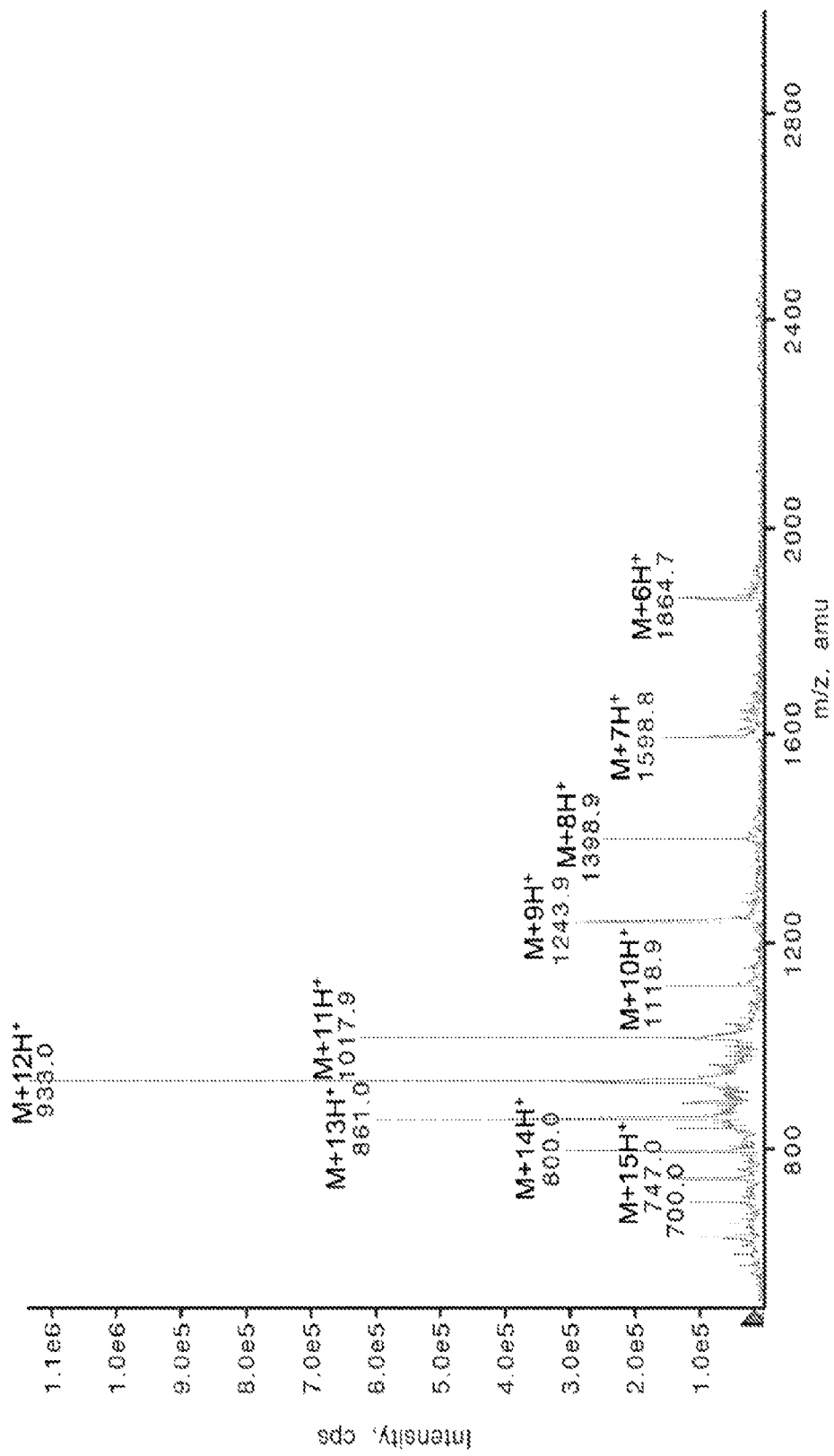
FIG. 9 is the ESI MS of H4R23C

To the protein solution (2 µg histone in 30 µL) in an Eppendorf tube, 10 µL of NuPAGE® 4×LDS sample buffer and 4 µL of 500 mM DTT were added. The sample was incubated at room temperature for 10 min but not boiled in order to minimize potential dephosphorylation of histidines. The solution was loaded onto 15% Tris-HCl Criterion (Bio-Rad) polyacrylamide gel and resolved by electrophoresis. Proteins were transferred to a PVDF membrane using Towbin buffer (192 mM glycine, 25 mm Tris-HCl, 10% methanol, pH 8.3) supplemented with 0.02% SDS. The western blot was performed using purified rabbit polyclonal antisera (1:1000, Active Motif) raised against peptide 13. A goat anti-rabbit IgG-HRP conjugate (1:5000, BioRad) was used as the secondary antibody, and the blot was visualized using Western Lighting ECL kit (Perkin Elmer). Then the blot was stripped and re-probed against an α-histone H4 antibody (1:7500, gift from Prof. David Allis at Rockefeller University). The Western blot of the recombinant histine H4 is depicted in FIG. 5.

The Western blot analysis clearly show that Ab-3-pHis selectively recognizes the histidine-phosphorylated histone H4, but not the non-phosphorylated counterpart.

It is to be noted that acid treatment of the phosphorylated histone affords the non-phoshoylated histone and abolishes this antibody recognition.

Since histine H4 has two histidines, (His-15 and His 75), mutant histone lacking histidines were prepared and tested. Experiments using these mutants show that Ab-2pHis selectively recognizes the phosphorylation of His 18 residue. This is the first example of an antibody that selectively recognizes a pHis containing protein.

Example 12

Native Chemical Ligation Between 19 and 20 pHis 10 analog was used in the SPPS of an α-thioester peptide, in preparing proteins via native chemical ligation. The semisynthesis of full-length Tn histone H4 was prepared. Since histone H4 does not have a native C45, a recombinant fragment of the protein with an N-terminal Cys (H1 A1-22 R2 3C 17) was chosen as the ligation partner.

In an Eppendorf tube, 2 mg of H4(Δ1-22)R23C (20) was dissolved 300 µL of ligation buffer (6 M guanidine, 200 mM sodium phosphate, pH 7.0, degassed by purging with argon for 15 min) 15 µL of 1 M TCEP solution (adjusted to pH 7 with 5N NaOH) and 15 µL of 1 M mercaptophenylacetic acid (MPAA) solution were added to the protein solution. Thioester peptide 19 (1.1 mg) was added and the tube was sealed under argon atmosphere. The mixture was then incubated at room temperature for 18 h until analytical HPLC analysis indicated the complete conversion. The reaction mixture was directed purified by semi-preparative RP-HPLC (35-70% B over 40 min, 4 mL/min) to give the desired ligation product 21 (1.4 mg, 58%) after lyophilization. See Scheme 3 below.

Scheme 3

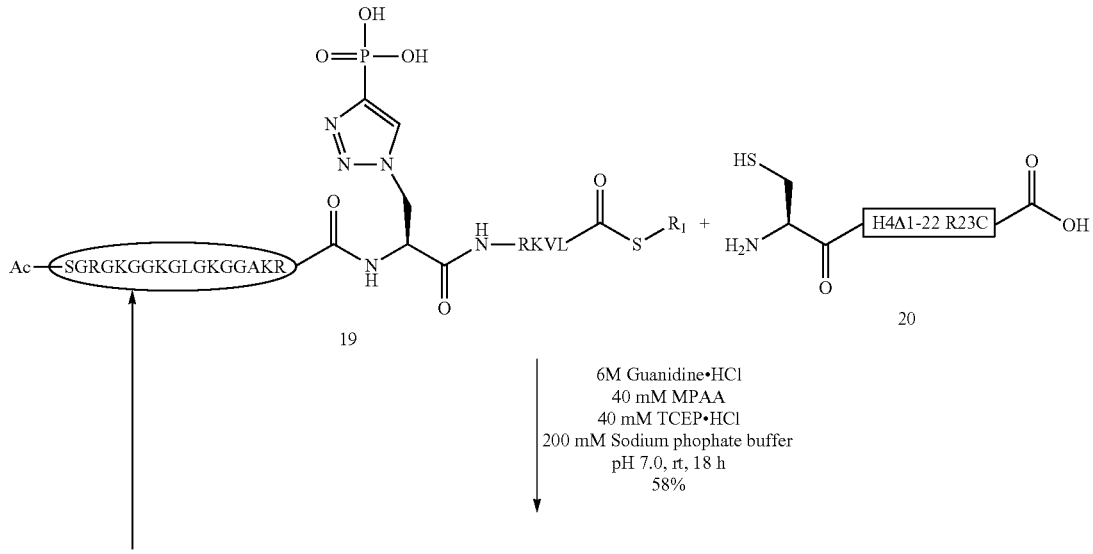

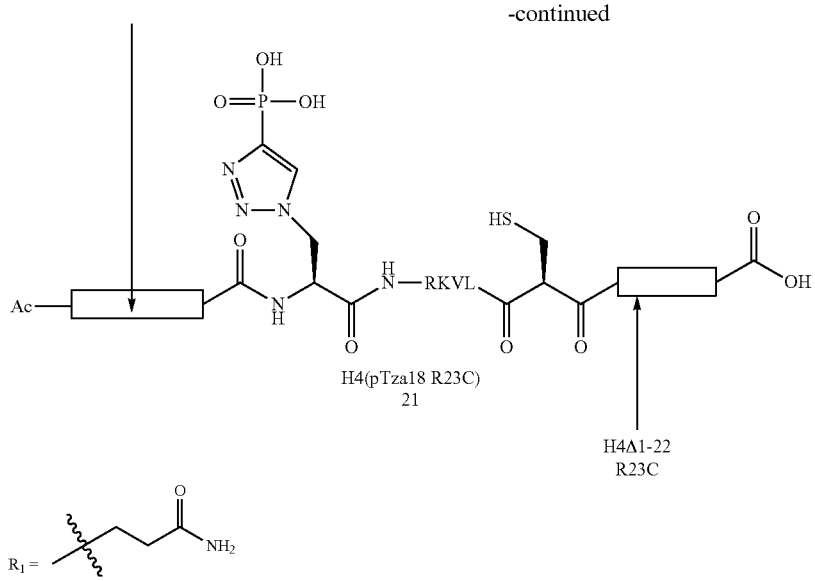

H4(pTza18 R23C)
21

H4Δ1-22
R23C where H4A1-22R23C is

CDNIQGITKPAIRRLARRGGVRISGLIYEETRGVLKVFLENVIRDAVTYT

EHAKRKTVTAMDVVYALKRQGRTLYGEGG 20 is assigned Sequence ID #22

Figure 4A:
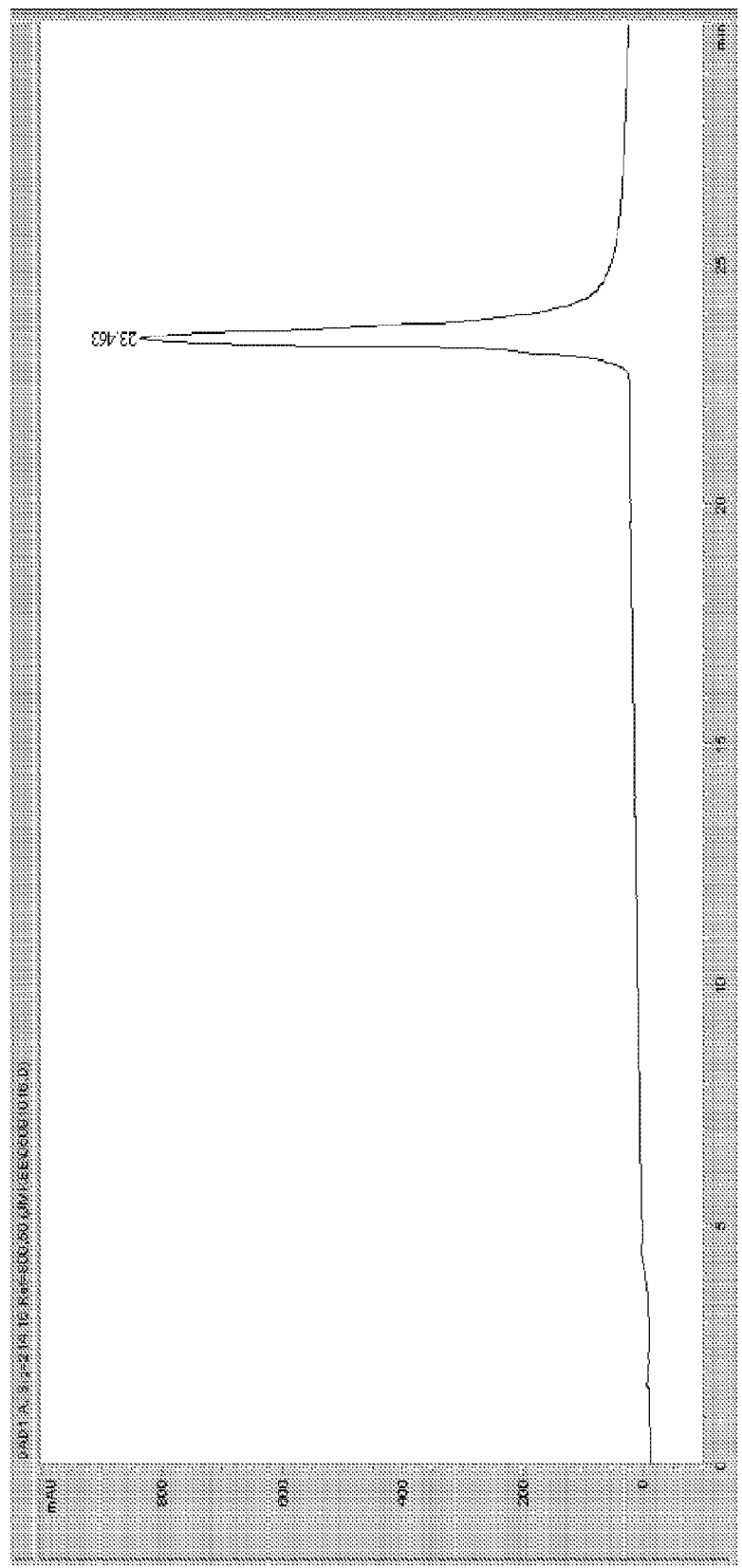
FIGS. 4A and 4B show shows the analytical data for peptide 21.
Figure 4B:
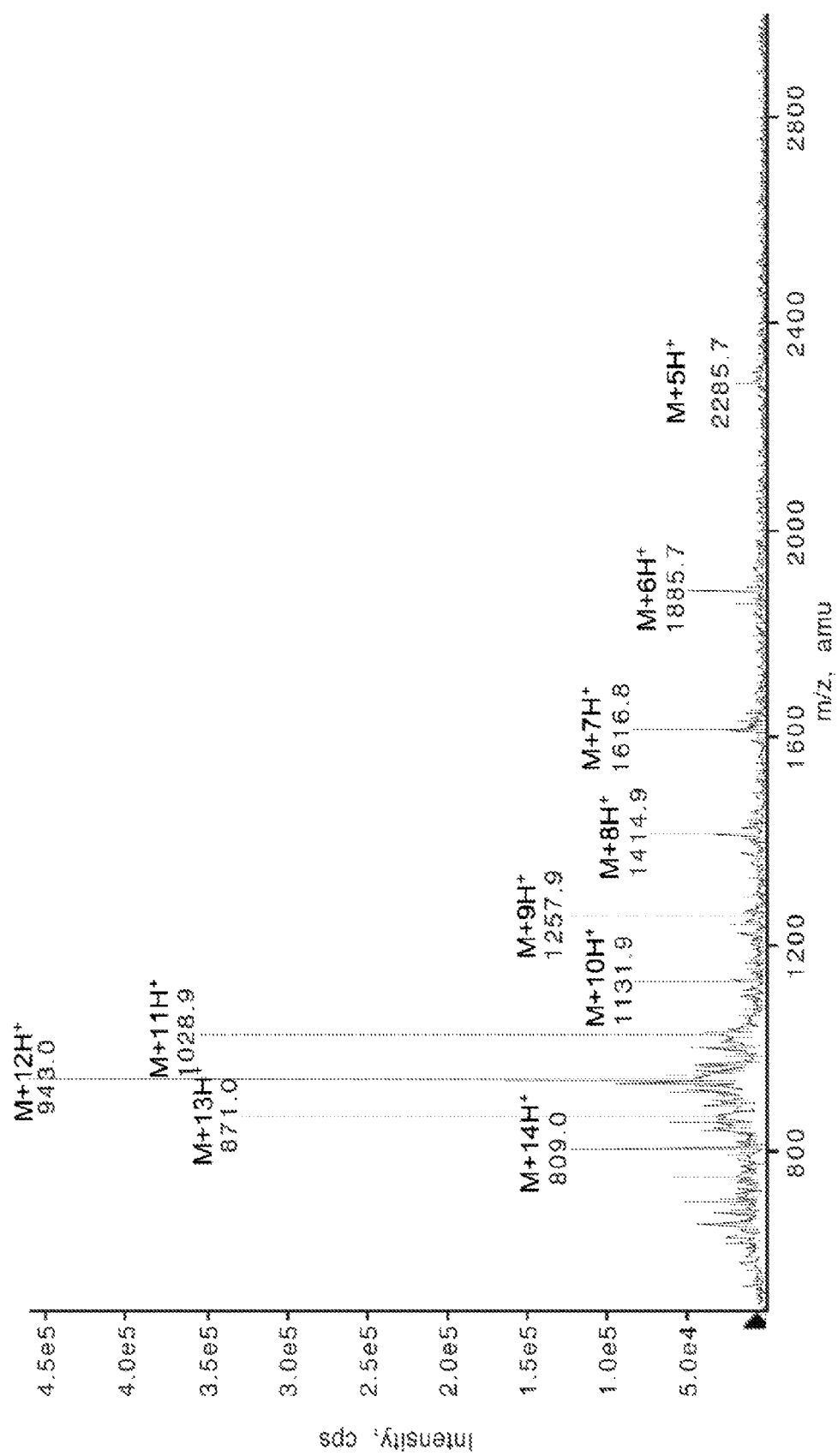

The analytical data for 21 (Sequence ID #23) is given in FIGS. 4A and 4B.

The native chemical ligation between thioester 19 and recombinant H4 fragment 20 proceeded smoothly, affording the desired full length histone H4 (18) in milligram quantities following purification antibody. The Western blot analysis is given in FIG. 5 and it shows that Ab 3pHis selectively recognizes 21 over the H4R23C mutant, again corroborating the specificity of the antibody.

Example 13

Preparation of Monoclonal Antibodies

The hapten(s), and fragments thereof, of the described invention are employed as immunogens in generating monoclonal antibodies by conventional techniques, e.g., techniques described in U.S. Pat. No. 5,599,905, hereby incorporated by reference. Additional techniques are known in the art, for example, the RIMMS (Repetitive Immunizations Multiple Sites) strategy (Kilpatrick et al., Hybridoma 16(4): 381-9; 1997.) It is recognized that polypeptides in various forms may be employed as immunogens, e.g., full length proteins, fragments thereof, fusion proteins such as Fc fusions, cells expressing the recombinant protein on the cell surface, etc.

For example, a hapten, or fragment thereof, of the described invention is conjugated to an antigenicity conferring carrier material (for example, but not limited to, a protein, a protein fragment, a synthetic polypeptide, or a semisynthetic polypeptide) to yield an immunogen. For a first immunization, 100 micrograms of immunogen (containing 50 micrograms of peptide) is emulsified in complete Freund's adjuvant (CFA) at 1:1 ratio by volume and injected subcutaneously in a final volume of 200 microliters for each mouse.

Immunized animals are boosted three to four more times with additional immunogen to increase the antigen-specific response, at intervals of two to four weeks (although longer intervals may be employed). For example, a second injection of 50 micrograms of immunogen (containing 25 micrograms of peptide) mixed with incomplete Freund's adjuvant in a final volume of 200 ul is injected subcutaneously into each mouse about four weeks after the primary immunization. A third injection (20 micrograms of immunogen containing 10 micrograms of peptide mixed with an adjuvant such as Ribi adjuvant) may be given by subcutaneous and/or intraperitoneal route from about 14 to about 28 days after the second injection. If desired, a fourth injection (20 micrograms of immunogen containing 10 micrograms of peptide mixed with incomplete Freund's adjuvant) may be given by subcutaneous and/or intraperitoneal route from about 14 to about 28 days after the third injection. A final injection is given, usually about five days prior to fusion, utilizing 50 micrograms of immunogen containing 25 micrograms of peptide in PBS, by intraperitoneal injection.

Serum samples are periodically taken by retro-orbital bleeding or tail-tip excision for testing by peptide ELISA (enzyme-linked immunosorbent assay), or another suitable assay, to evaluate antibody titer. At the time of fusion, the animals are sacrificed, splenocytes harvested, and fused to the murine myeloma cell line SP2/O (ATCC CRL 1581) or another suitable cell line, several of which are known in the art. The resulting hybridoma cell lines are plated in multiple microtiter plates in a HAT selective medium (hypoxanthine, aminopterin, and thymidine) to facilitate proliferation of spleen cell-myeloma hybrid cells.

Hybridoma clones thus generated are screened for reactivity with the immunogen of the described invention. Initial screening of hybridoma supernatants may utilize a peptide ELISA, a whole cell ELISA and/or a cell-based assay suitable for high-throughput screening (fluorometric microvolume assay technology or FMAT, substantially as described by Fiscella, et al., Nature Biotechnology 21:302-307; 2003). Hybridomas that are positive in this screening method may be further cultured to provide larger amounts of antibody, which can then be purified as described below and screened by additional cell-based assay(s).

Selected hybridomas may be further cloned and tested to ensure stable production of monoclonal antibody. Hybridomas can be cultured in vitro, or passaged as ascites fluid in suitable host mammals. The resulting monoclonal antibodies may be purified by ammonium sulfate precipitation followed by gel exclusion chromatography, and/or affinity chromatography based on binding of antibody to Protein G, for example. Several hybridomas can be generated and tested for binding in a whole-cell ELISA using the immunogen, expressing cells, and in a flash plate assay.

Example 14

Purification of Anti-Immunogen Hybridoma Antibodies for Screening

Hybridoma cells are cultured for a time and under conditions to yield a sample of about 35 ml of hybridoma supernatant fluid. To each sample is added 12 ml of 4×-Protein A Binding Buffer (1.6 M citric acid, 100 mM tris, pH 9.15) and about 300 μl of a 67% slurry of MabSelect™ Media (GE Healthcare, Piscataway, N.J.). The resulting slurry is rotated gently over night at 4° C.

After overnight incubation, the samples are centrifuged to sediment the resin and the monoclonal antibodies bound thereto, for example at 2,000 RPM in a G3.8 centrifuge rotor (Beckman Coulter, Fullerton, Calif.) for 5 minutes at 4° C. with no brake. All but about 300 μl of the supernatant fluid is removed and the resin is resuspended to form a concentrated slurry.

The concentrated slurry is transferred to a microcentrifuge tube and sufficient 1×-Protein A Binding Buffer (400 mM citric acid, 25 mM tris, pH 8.9) is added to bring the total volume up to about 1 ml. The slurry is resuspended, then centrifuged at about 14,000 g for 5 seconds. The supernatant fluid is removed from the resulting pellet, which is washed a total of three times in a similar manner (i.e. by resuspending in about 1 ml of 1×-Protein A Binding Buffer, centrifuging, removing supernatant and resuspending in fresh buffer).

After three washes, the pellet is resuspended in 400 μl Elution Buffer (200 mM formic acid) and agitated for 10 min at room temperature, then centrifuged at 14,000 g for 5 seconds. The supernatant is carefully removed as eluate, and the pellet is eluted again in a manner similar to that described above for a total of three elution cycles. The eluates from the three elution cycles are combined, centrifuge at 14,000 g for 5 min room temperature and transferred to a fresh tube. The pH is adjusted to 7.8-8.2 by adding 2 M tris base (235 mM$_f$) and mixing quickly. The samples are again centrifuged at 14,000 g for 5 min at room temperature, and designated as pH Shift Soluble. A spectral scan of each sample (diluted by adding 20 μl of the sample to 700 μl water) is run from 250 to 350 nm, and protein concentration is verified by loading 0.5 μg each antibody-containing sample on a reducing 4-20% SDS-PAGE gel with an appropriate antibody standard.

Example 15

Purification and Western Blot of Immunogen/Fc Polypeptide

Full length Immunogen/Fc polypeptide is expressed in CHO cells. Full length proteins are purified using MabSelect™ resin substantially as previously described (see Example 2). The resultant purified Fc-constructs are analyzed by amino terminal sequence analysis (Edman degradation), size exclusion chromatography, absorbance spectral scan, and mass spectroscopy.

Various amounts of purified full length Immunogen-Fc are subjected to SDS-PAGE using 8-16% polyacrylamine gradient gels (Novex gels, Invitrogen Life Technologies) in a Tris-Glycine buffer system. Gel lanes containing See Blue standards (Novex, Invitrogen Life Technologies) for molecular weight identification are also included. Following electrophoresis, proteins are transferred from gels onto nitrocellulose membranes using a Novex XCell II Blot Module (Invitrogen Life Technologies). Membranes are blocked with 1:1, Odyssey blocking buffer, OBB, (LI-COR Biosciences):TBS (Tris Buffer Saline) overnight at 4° C. with shaking. Antibodies to be analyzed are diluted in 1:1 OBB:TBS at a desired final concentration for 1 hr at room temperature. Membranes are washed extensively with 0.1% Tween 20 in TBS (3-4 changes of 100 ml over about 1 hr). Membranes are then exposed to the appropriate secondary antibody-Alexa680 (Molecular Probes, Invitrogen Life Technologies) conjugate (goat anti-rabbit IgG, or goat anti-mouse IgG) diluted 1:5000 in 1:1 (OBB:TBS) for 1 hr at room temperature. Membranes are washed as described above, and if desired, analyzed using a LI-COR Odyssey Infrared Imaging System (LI-COR Biosciences).

Each reference cited in EXAMPLES 13-15 herein is incorporated by reference in its entirety for all that it teaches and for all purposes.

In the present application, unless indicated to the contrary, the singular denotes the plural and vice versa.

In addition, the abbreviation pHis refers to a phosphorylated histidine. Moreover, the abbreviation pTza refers to phosphono triazolylalanine of Formula I.

Furthermore, unless indicated to the contrary, % is by weight.

The above preferred embodiments and examples are given to illustrate the scope and spirit of the present invention. The embodiments and examples described herein will make apparent to those skilled in the art other embodiments and examples. These other embodiments and examples are within the contemplation of the present invention. Therefore, the present invention should be limited only by the appended claims.

What is claimed in:

1. An isolated antibody that specifically recognizes a phosphohistidine or a phosphopolypeptide having at least one histidine thereon which is phosphorylated, said antibody does not recognize a non-phosphorylated histidine, other phosphoamino acids and polypeptide which does not have a phosphorylated histidine.

2. The isolated antibody according to claim 1 wherein the antibody is raised against a hapten having the formula:

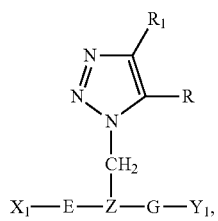

wherein $X_1$ and $Y_1$ are independently a bond,

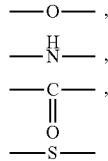

or a salt thereof wherein

Z is CH, N or $SiR_{11}$;

$R_{11}$ is an alkyl group or H,

E and G are independently a chemical bond or a linker group selected from the group consisting of alkyl, alkenyl, alkynyl, cycloalkyl, cycloalkylalkyl, cycloalkenyl, cycloalkenyl alkyl, heterocyclic, heterocyclic alkyl, (O—$CH_2$—$CH_2$)n, and ($CH_2$)q wherein one of the $CH_2$ groups is replaced by O, n is 1-100;

q is 1-6;

one of R and $R_1$ is H and the other is

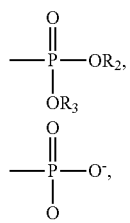

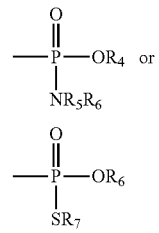

and $R_2$, $R_3$, $R_4$, $R_5$, $R_6$, and $R_7$ are independently hydrogen, alkyl, alkenyl, cycloalkyl, aryl, cycloalkylalkyl, aryl alkyl, heterocyclic, or heterocyclicalkyl.

3. The isolated antibody according to claim 2 wherein E and G are both a chemical bond.

4. The isolated antibody according to claim 2 wherein $X_1$ is

and $Y_1$ is

or $Y_1$ is

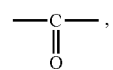

and $X_1$ is

.

5. The isolated antibody according to claim 3 wherein $X_1$ is

and $Y_1$ is

or $Y_1$ is

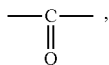

and $X_1$ is

6. The isolated antibody of claim 1 wherein the antibody is a monoclonal or polyclonal antibody.

7. The isolated antibody of claim 1 which is a humanized form thereof, a chimeric form thereof or a fragment thereof.

8. The isolated antibody according to claim 2 wherein the hapten has the formula

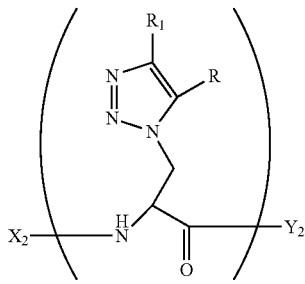

wherein $X_2$ is linked to the NH group and $Y_2$ is linked to the carbonyl group of the structure which is shown within the parenthesis, and where one of $R_1$ and R is

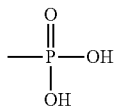

or anion thereof and the other is 1-1 and $Y_2$ is OH or an amino acid residue of 1-15 amino acids and $X_2$ is H, an amino acid residue of 1-15 amino acids wherein the amino acids are selected from the group consisting of Gly, Ala, Val, Leu, Ile, Asp, Glu, Asn, Gln, Lys, His, Pro, Phe, Trp, Tyr, Ser, Thr, Met, Cys and Arg, or

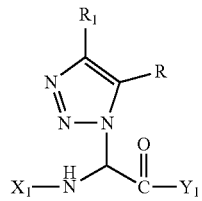

wherein $X_1$ is a bond or H and $Y_1$ is a bond or OH and wherein the sum of the amino acid residues in $X_2$ and $Y_2$ ranges from 1 to about 200.

9. The isolated antibody of claim 2 wherein the hapten is comprised of a phosphoryltriazole fragment having the structure

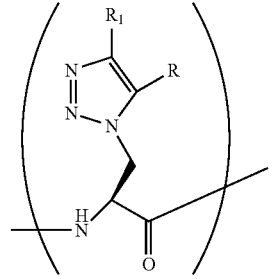

10. The isolated antibody according to claim 2 wherein the hapten has an amino acid sequence selected from SEQ. ID NO. 1-8, 12, 13, 18, and 23.

11. The isolated antibody according to claim 10 wherein the hapten has the amino acid sequence of SEQ ID NO. 12.

12. An antibody fragment of the isolated antibody of claim 1, wherein the antibody fragment is selected from the group consisting of Fab, Fab', F(ab')$_2$, and Fc fragments; diabodies; linear antibodies; and single-chain antibody molecules.

13. A composition comprising the isolated antibody of claim 1.

14. A composition comprising the isolated antibody of claim 6.

15. A composition comprising the isolated antibody of claim 7.

* * * * *